United States Patent
Holaday et al.

(10) Patent No.: US 6,773,669 B1
(45) Date of Patent: Aug. 10, 2004

(54) FLOW ELECTROPORATION CHAMBER AND METHOD

(75) Inventors: John W. Holaday, Bethesda, MD (US); Peter H. Meserol, Montville, NJ (US); Doug Doerfler, Darnestown, MD (US); Shawn J. Green, Vienna, VA (US); Vininder Singh, Gaithersburg, MD (US)

(73) Assignee: Maxcyte, Inc., Rockville, MD (US)

( * ) Notice: Subject to any disclaimer, the term of this patent is extended or adjusted under 35 U.S.C. 154(b) by 0 days.

(21) Appl. No.: 09/707,928

(22) Filed: Nov. 8, 2000

Related U.S. Application Data

(63) Continuation of application No. 09/397,303, filed on Sep. 15, 1999, now abandoned, which is a continuation-in-part of application No. 08/627,843, filed on Mar. 11, 1996, now Pat. No. 6,074,605, which is a continuation-in-part of application No. 08/402,145, filed on Mar. 10, 1995, now Pat. No. 5,720,921

(60) Provisional application No. 60/004,906, filed on Oct. 6, 1995.

(51) Int. Cl.⁷ .............................................. C12N 15/87
(52) U.S. Cl. ........................ 422/44; 422/33; 435/173.6
(58) Field of Search ........................... 435/172.3, 173.6; 422/44, 33

(56) References Cited

U.S. PATENT DOCUMENTS

| | | | |
|---|---|---|---|
| 2,955,076 A | 10/1960 | Gossling | |
| 3,676,325 A | 7/1972 | Smith et al. | 204/288 |
| 4,075,076 A | 2/1978 | Xylander | 204/206 |
| 4,081,340 A | 3/1978 | Zimmermann et al. | 204/180 |
| 4,192,869 A | 3/1980 | Nicolau et al. | 424/199 |
| 4,252,628 A | 2/1981 | Boulton et al. | 204/257 |
| 4,321,259 A | 3/1982 | Nicolau et al. | 424/101 |
| 4,370,983 A * | 2/1983 | Lichtenstein | 128/630 |
| 4,440,386 A | 4/1984 | Achelpohl | 271/70 |
| 4,473,563 A | 9/1984 | Nicolau et al. | 424/224 |
| 4,476,004 A | 10/1984 | Pohl | 204/299 |
| 4,478,824 A | 10/1984 | Franco et al. | 424/101 |
| 4,622,302 A | 11/1986 | Sowers | 435/172.2 |
| 4,652,449 A | 3/1987 | Ropars et al. | 424/101 |
| 4,663,292 A | 5/1987 | Wong et al. | 435/287 |
| 4,695,547 A | 9/1987 | Hilliard et al. | 435/173 |
| 4,699,881 A | 10/1987 | Matschke | 435/173 |
| 4,752,586 A | 6/1988 | Ropars et al. | 435/287 |
| 4,764,473 A | 8/1988 | Matschke et al. | 435/287 |
| 4,784,737 A | 11/1988 | Ray et al. | 204/180.1 |
| 4,800,163 A | 1/1989 | Hibi et al. | 435/287 |

(List continued on next page.)

FOREIGN PATENT DOCUMENTS

| | | |
|---|---|---|
| AT | 680890 | 10/1994 |
| CA | 2214800 | 2/2002 |
| CN | 1195997 | 10/1998 |

(List continued on next page.)

OTHER PUBLICATIONS

"Advanced Coatings for the Medical Industry," Multi–Arc Scientific Coatings, Copyright © AAndal Corp.

"Biological Buffers," In: *The Biological Engineering Handbook*, Bronzino (ed.) CRC Press, pp. 1650, c1995.

(List continued on next page.)

*Primary Examiner*—Dave T. Nguyen
(74) *Attorney, Agent, or Firm*—Fulbright & Jaworski, LLP

(57) ABSTRACT

The present invention relates to a method and apparatus for the encapsulation of substances and drugs into cells and platelets. The present invention is also related to the incorporation of thrombus dissolving drugs, such as tissue plasminogen activator and streptokinase into platelets using the apparatus described herein. The treated platelets can then be used to treat patients suffering from a thrombus blocking a blood vessel. The present invention is also related to a preparation of red blood cells that has a stable right shift of the oxygen dissociation curve.

19 Claims, 18 Drawing Sheets

U.S. PATENT DOCUMENTS

| | | | |
|---|---|---|---|
| 4,804,450 A | 2/1989 | Mochizuki et al. | 204/299 |
| 4,822,470 A | 4/1989 | Chang | 204/299 |
| 4,840,714 A | 6/1989 | Littlehales | 204/180.1 |
| 4,849,089 A | 7/1989 | Marshall, III | 204/299 |
| 4,849,355 A | 7/1989 | Wong | 435/172.3 |
| 4,874,690 A | 10/1989 | Goodrich, Jr. et al. | 435/2 |
| 4,882,281 A | 11/1989 | Hilliard et al. | 435/287 |
| 4,906,576 A | 3/1990 | Marshall, III | 435/287 |
| 4,910,140 A | 3/1990 | Dower | 435/172.3 |
| 4,923,814 A | 5/1990 | Marshall, III | 435/173 |
| 4,931,276 A | 6/1990 | Franco et al. | 424/533 |
| 4,945,050 A | 7/1990 | Sanford et al. | 435/172.1 |
| 4,946,793 A | 8/1990 | Marshall, III | 435/291 |
| 4,956,288 A | 9/1990 | Barsoum | 435/172.3 |
| 4,970,154 A | 11/1990 | Chang | 435/172.2 |
| 4,995,268 A * | 2/1991 | Ash | 73/861.05 |
| 4,995,957 A | 2/1991 | Ziegler et al. | 204/182.8 |
| 5,007,995 A | 4/1991 | Takahashi et al. | 204/299 |
| 5,036,006 A | 7/1991 | Sanford et al. | 435/170.1 |
| 5,043,261 A | 8/1991 | Goodrich et al. | 435/2 |
| 5,098,843 A * | 3/1992 | Calvin | |
| 5,100,627 A | 3/1992 | Buican et al. | 422/108 |
| 5,100,792 A | 3/1992 | Sanford et al. | 435/172.1 |
| 5,114,681 A | 5/1992 | Bertoncini et al. | 422/111 |
| 5,124,259 A | 6/1992 | Tada | 435/172.1 |
| 5,128,257 A | 7/1992 | Baer | 435/173 |
| 5,134,070 A | 7/1992 | Casnig | 435/173 |
| 5,135,667 A | 8/1992 | Schoendorfer | 210/782 |
| 5,137,817 A | 8/1992 | Busta et al. | 435/173 |
| 5,139,684 A | 8/1992 | Kaali et al. | 210/748 |
| 5,232,856 A | 8/1993 | Firth | 435/287 |
| 5,424,209 A | 6/1995 | Kearney | 435/284 |
| 5,501,662 A | 3/1996 | Hofmann | 604/20 |
| 5,545,130 A | 8/1996 | Hofmann et al. | 604/4 |
| 5,612,207 A * | 3/1997 | Nicolau et al. | |
| 5,676,646 A * | 10/1997 | Hofmann et al. | |
| 5,720,921 A * | 2/1998 | Meserol | |
| 5,728,281 A | 3/1998 | Holmström et al. | 204/403 |
| 6,074,605 A * | 6/2000 | Meserol et al. | |
| 6,090,617 A | 7/2000 | Meserol | 435/285.2 |
| 6,485,961 B1 | 11/2002 | Meserol | 435/285.2 |
| 2001/0001064 A1 | 5/2001 | Holaday | 435/173.6 |

FOREIGN PATENT DOCUMENTS

| | | |
|---|---|---|
| DE | 2405119 | 9/1975 |
| DE | 3603029 | 8/1987 |
| DE | 4440386 | 5/1996 |
| EP | 0137504 | 4/1985 |
| EP | 0343783 | 11/1989 |
| EP | 0362758 | 4/1990 |
| EP | 0472772 | 3/1992 |
| EP | 0798309 | 10/1997 |
| JP | 62151174 | 7/1987 |
| JP | 62171687 | 7/1987 |
| JP | 62228277 | 10/1987 |
| JP | 62265975 | 11/1987 |
| JP | 63141587 | 6/1988 |
| JP | 1141582 | 6/1989 |
| JP | 2131584 | 5/1990 |
| JP | 2131585 | 5/1990 |
| JP | 2186993 | 7/1990 |
| JP | 3195485 | 8/1991 |
| JP | 4027393 | 1/1992 |
| JP | 6349068 | 12/1994 |
| JP | 7180029 | 7/1995 |
| JP | 7320720 | 12/1995 |
| WO | WO 88/04322 | 6/1988 |
| WO | WO 89/02464 | 3/1989 |
| WO | WO 89/03426 | 4/1989 |
| WO | WO 91/18103 | 11/1991 |
| WO | WO 94/21117 * | 9/1994 |
| WO | WO 96/28199 | 3/1996 |
| WO | WO 98/24490 | 6/1998 |
| WO | WO 01/24830 | 4/2001 |

OTHER PUBLICATIONS

"Ion Bond® 16 Zirconium Nitride Coating," Multi–Arc., 1996.

"Ion Bond® 17 Titanium Aluminum Nitride Coating," Multi–Arc, Inc., 1995.

"Ion Bond® 19 Chromium Nitride Coating," Multi–Arc, Inc., 1995.

"Ion Bond® Coatings for Instruments, Design Considerations," Multi–Arc, Inc., 1995.

"Ion Bond® Coatings for Instruments, Most Commonly Asked Questions," Multi–Arc, Inc., 1995.

"Preparation of certain reagents, anticoagulants and preservative solutions," In: *Practical Haematology*, 5$^{th}$Edition, Dacie and Lewis (eds.), Appendicies, pp. 598, 1975.

"The Ion Bond Network," Multi–Arc, Inc., 1995.

Abatti et al., "Development of a new geometrical form of micropipette: electrical characteristics and an application as a potassium ion selective electrode," *IEEE Trans. Biomed. Eng.*, 39:43–48, 1992.

Asakami et al., "Materials for electrode of alkali metal thermoelectric converter (AMTEC) (II),"*J. Mater. Sci. Lett.*, 9(8):892–894, 1990.

Behrndt and Lunk, "Biocompatibility of TiN preclinical and clinical investigations," *Materials Sciences & Engineering*, A139:58–60, 1991.

Capizzi et al., "Amifostine mediated protection of normal bone marrow from cytotoxic chemotherapy," *Cancer*, 72:3495–3501, 1993.

Chassy et al., "Transformation of bacteria by electroporation," *Trends in Biotechnology*, 6(12):303–309, 1988.

Coll et al., "Metallurgical and Tribological modification of titanium and titanium alloys by plasma assisted techniques," *Workshop H Society for Biomaterials Implat Retrieval Symposium*, Sep. 17, 1992.

Dunican and Shivnan, "High frequency tranformation of whole cells of amino acid producing coryneform bacteria using high voltage electroporation," *Bio/Technology*, 7:1067–1070, 1998.

Egorov and Noikova, "Effect of phase composition of TiN–Ni sintered electrode materials of characteristics of the ESA process," *Sov. Powder Metall Met. Ceram.*, 29(9):705–710, 1991.

Einck and Holaday, "Enhancement of tissue oxygenation by intracellular introduction of inositol hexaphosphate by flow electroporation of red blood cells," In: *Tissue Oxygenation in Acute Medicine (Update in Intensive Care and Emergency Medicine, 33)*, Sibbald et al., (eds.), pp. 357–374, c1998.

Gersonde and Nicolau, "Enhancement of to $O_2$release capacity and of the Bohr–effect of human red blood cells after incorporation of inositol hexaphosphate by fusion with effector–containing lipid vesicles," In: *Origins of Cooperative Binding by Hemoglobin*, 277–282, 1982.

Gersonde and Nicolau, "Improvement of the red blood cell $O_2$ release capacity by lipid vesicle–mediated incorporation of inositol hexaphosphate, " *Blut*, 39:1–7, 1979.

Gersonde and Nicolau, "Modification of the oxygen affinity of intracellular haemoglobin by incorporation of polyphosphates into intact red blood cells and enhanced $O_2$ release in the capillary system," *Biblthca Haemat.*, 46:81–92, 1980.

Gersonde and Weiner, "The influence of infusion rate on the acute intravenous toxicity of phytic acid, a calcium–binding agent," *Toxicology*, 22:279–286, 1982.

Hirai et al., "A new antitumor antibiotic, FR–900482" *J. of Antibiotics*, 40/5:607–611, 1987.

Hoffmann and Evans, "Eletronic genetic—Physical and biological aspects of cellular electromanipulation," *IEEE Engineering in Medicine and Biology Magazine*, 6–11, 19–22, 1986.

Kinosita and Tsong, "Voltage–induced conductance in human erythrocyte membranes," *Biochimica et Biophysica Acta*, 554:479–497, 1979.

Kobayashi et al., "Fabrication of zirconim nitride sintered bodies and the application for electrode materials," *J. Ceram. Soc. Jpn.*, 97(10):1189–1194, (with Engilsh summary), 1989.

Kullmann et al., "In vitro effects of pentoxifylline on smooth muscle cell migration and blood monocyte production of chemotactic activity for smooth muscle cells: potential therapeutic benefit in the adult respiratory distress syndrome," *Am J. Respir. Cell*, 8:83–88, 1993.

Kurtz and Gordon, "Transparent conducting electrodes on silicon," *Sol. Energy Mater.*, 15(4):229–236, 1987.

Lehninger (ed.), In: *Principles of Biochemistry*, Chapter 8: 181–194, 1982.

Maurer et al., "Reduction of fretting corrosion of Ti–6A1–4V by various surface treatments," *J. Orthop. Res.*, 11:865–873, 1993.

Merz et al., "Determination of HIV infection in human bone," *Unfallchirurg*, 941:47–49, (with English summary), 1991.

Mouneimne et al., "Stable rightward shifts of the oxyhemoglobin dissocation curve induced by encapsulation of inositol hexaphosphate in red blood cells using electroporation," *FEBS Letters*, 275:117–120, 1990.

Narayan et al., "Diamond, diamond–like and titanium nitride biocompatible coatings for human body parts," *Materials Sciences & Engineering*, B25:5–10, 1994.

Nicolau et al., "Incorporation of allosteric effectors of hemoglobin in red blood cells. Physiological effects," *Biblthca haemat.*, 51:92–107, 1985.

Nicolau et al., "Short– and long–term physiological effects of improved oxygen transport by red blood cells containing inositol hexaphosphate," In: *Phytic Acid: Chemistry and Applications*, Graf (ed.), Chapter 16:265–290, 1986.

Pietra et al., "Titanium nitride as a coating for surgical instruments used to collect human tissue for trace metal analysis," *Analyst*, 115:1025–1028, 1990.

Ropars et al., "Improved oxygen delivery to tissues and iron chelator transport through the use of lysed and resealed red blood cells: a new perspective on cooley's anemia therapy," *Annals New York Academy of Sciences*, 445:304–315, 1985.

Satomi et al., "Tissue response to implanted ceramic–coated titanium alloys in rats," *J. Oral Rehab.*, 15:339–345, 1988.

Schaldach et al., "Pacemaker electrodes made of titanium nitride," *Biomed. Technik.*, 34:185–190, 1989, with English abstract.

Shoji et al., "New fabrication process for Josephson tunnel junctions with (niobium nitride niobium) double–layered electrodes," *Appl. Phys. Lett.*, 41(11):1097–1099, 1982.

Susuki, "Biomedical electrode with silicon nitride film," *Jpn. J. Med. Electron. Biol.*, 19(2):114–119, (with English summary), 1981.

Taheri et al., "A dry electrode for EEG recording," *Electroencephalography and Clinical Neurophysiology*, 90(5):376–383, 1994.

Tait and Aita, "Aluminum nitride as a corrosion protection coating for steel: self–sealing porous electrode model," *Surf. Eng.*, 7(4):327–330, 1991.

Teisseire et al., "Physiological effects of high–$P_{50}$ erythrocyte transfusion on piglets," *J. Appl. Phys.*, 58:1810–1817, 1985.

Teisseire et al., "Significance of low hemoglobin oxygen affinity," 153–159, ??.

Teissere et al., "Long–term physiological effects of enhanced $O_2$ release by inositol hexaphosphate–loaded erythrocytes," *Proc. Natl. Acad. Sci., USA*, 84:6894–6898, 1987.

Therin et al., "A histomorphometric comparison of the muscular tissue reaction to stainless steel, pure titanium and titanium alloy implant materials," *J. Materials Science: Materials in Medicine*, 2:1–8, 1991.

Vasilenko et al., "Preparation of porous electrodes from titanium nitrides," *Poroshkovaia Metallurgiia*, 13:39–42, 1973, article in Russian, (with English summary).

Weiner, "Right shigting of Hb–$O_2$dissociation in viable red cells by liposomal technique," *Biol. of the Cell*, 47:65–70, 1983.

Weisel et al., "Adverse effects of transfusion therapy during abdominal aortic aneurysectomy," *Surgery*, 83:682–690, 1978.

Wisbey et al., "Application of PVD TiN coating to Co–Cr–Mo based surgical implants," *Biomaterials*, 8:477–480, 1987.

Wisbey et al., "Titanium release from TiN coated implant materials," *ImechE*, C384/042:9–14, 1989.

Zhao et al., "Direct current (dc)–plasma CVD equipment with auxiliary heating electrodes," *Vacuum*, 42(17):1109–1111, 1991.

Zhu et al., "Fabrication and characterization of glucose sensors based on a microarray hydrogen peroxide electrode," *Biosensors and Bioelectronics*, 9(4–5):295–300, 1994.

* cited by examiner

Fig_1

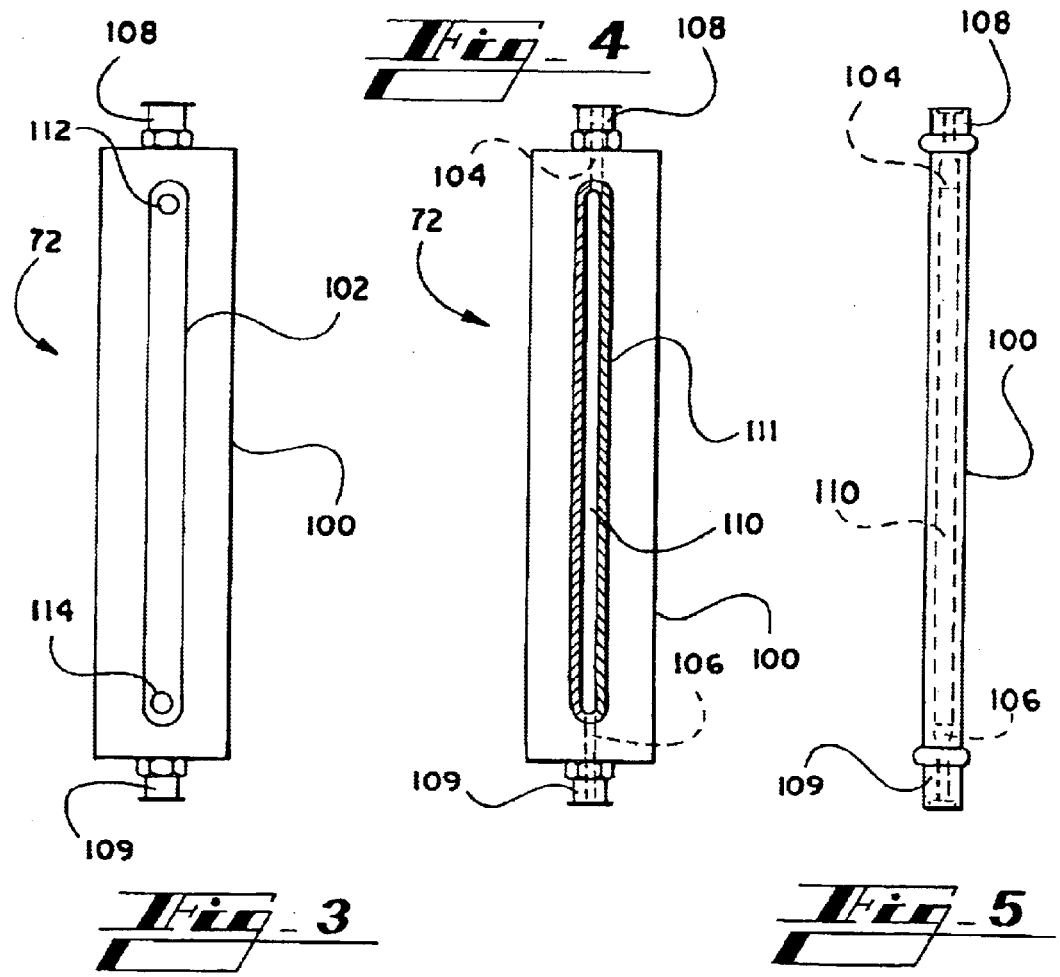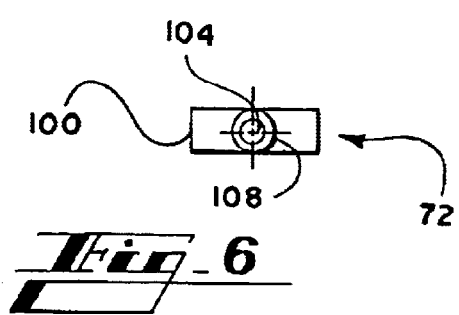

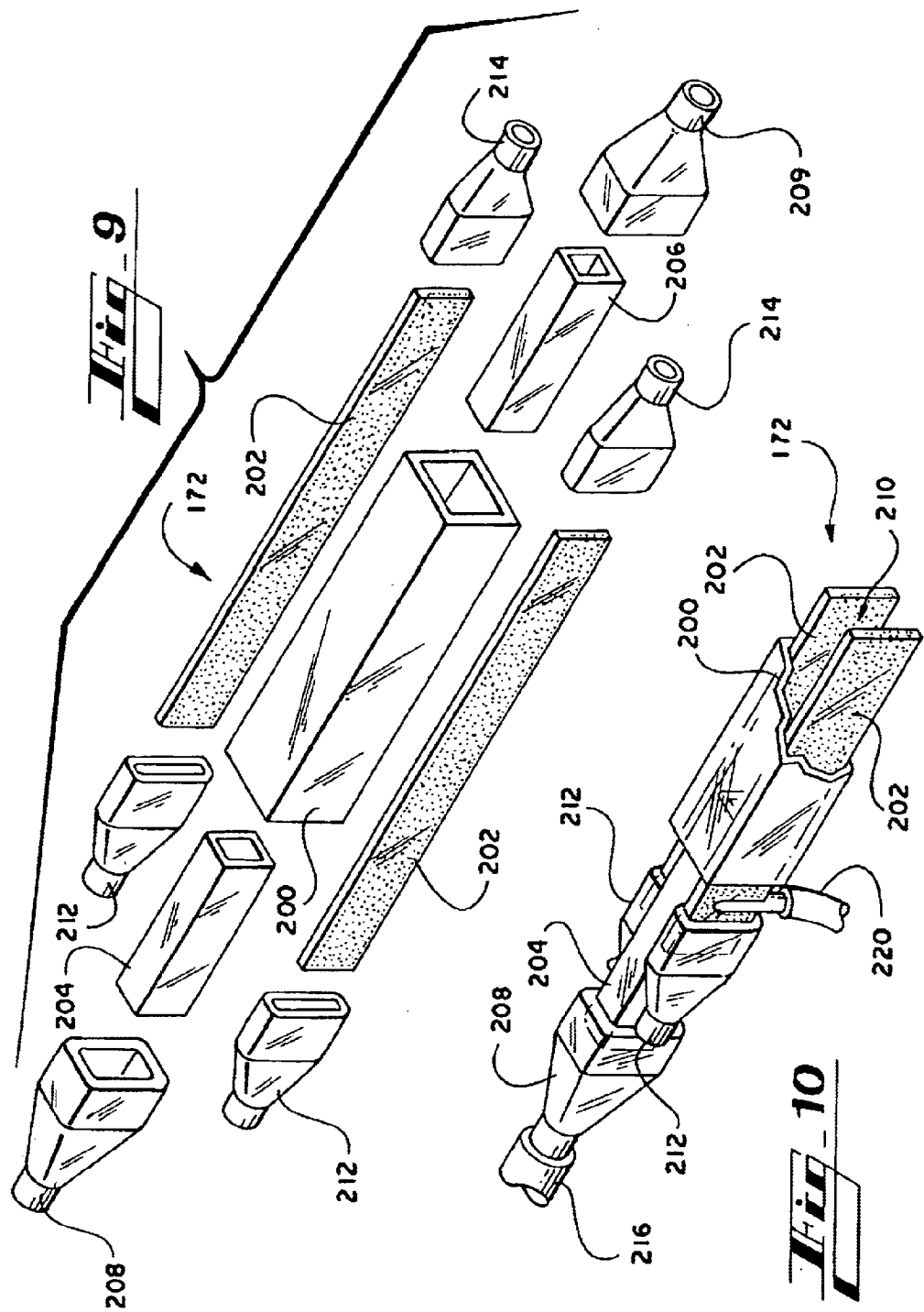

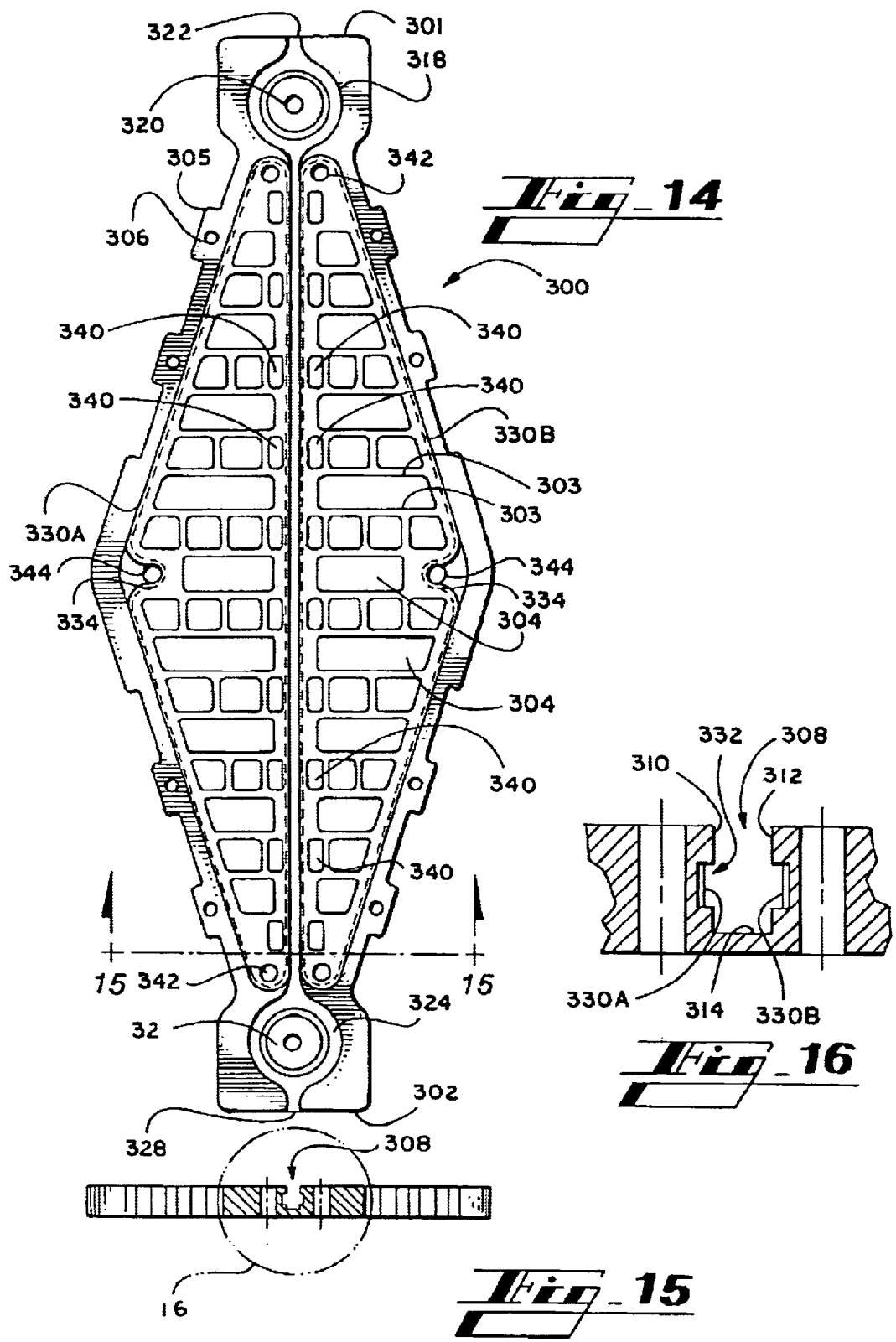

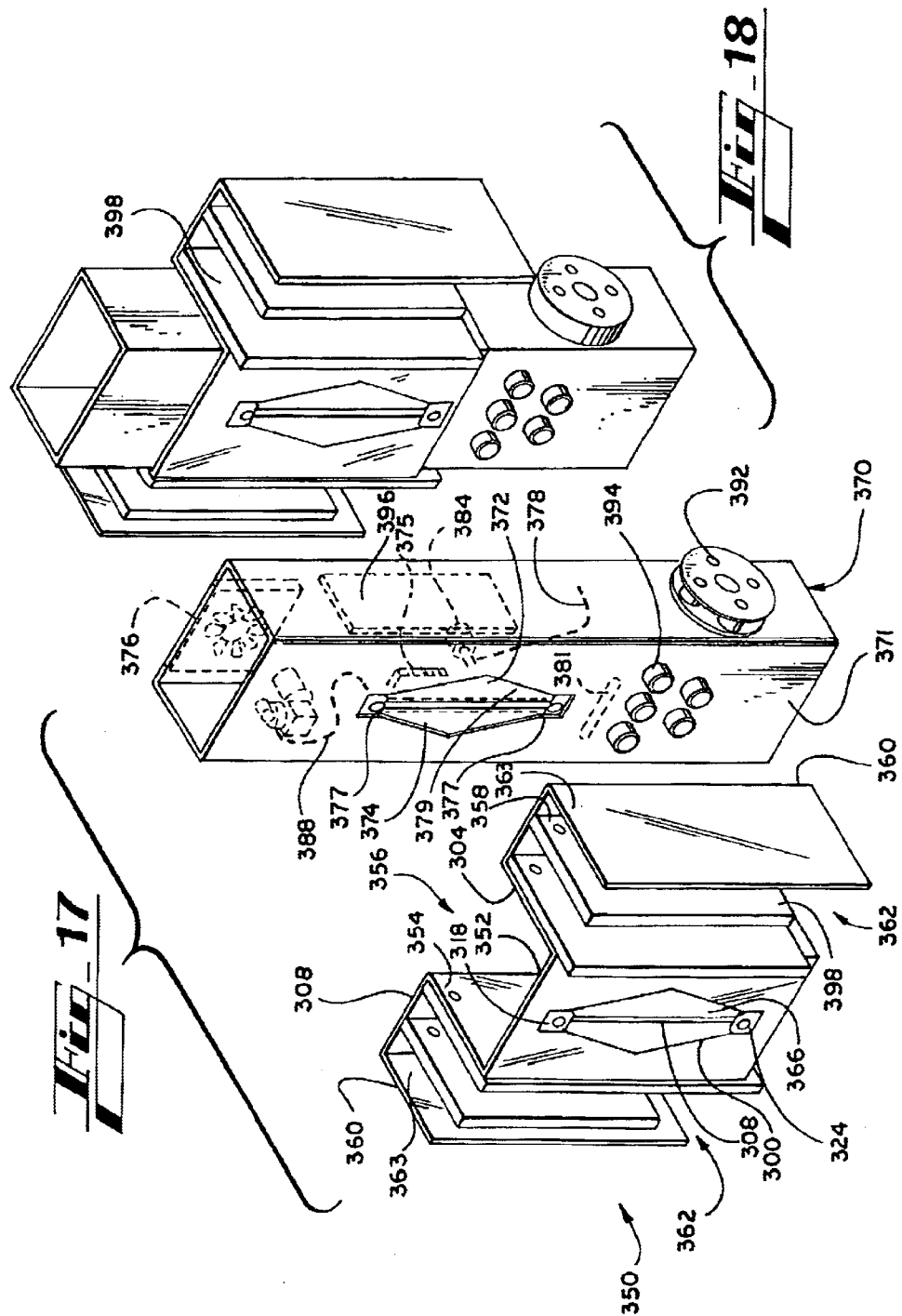

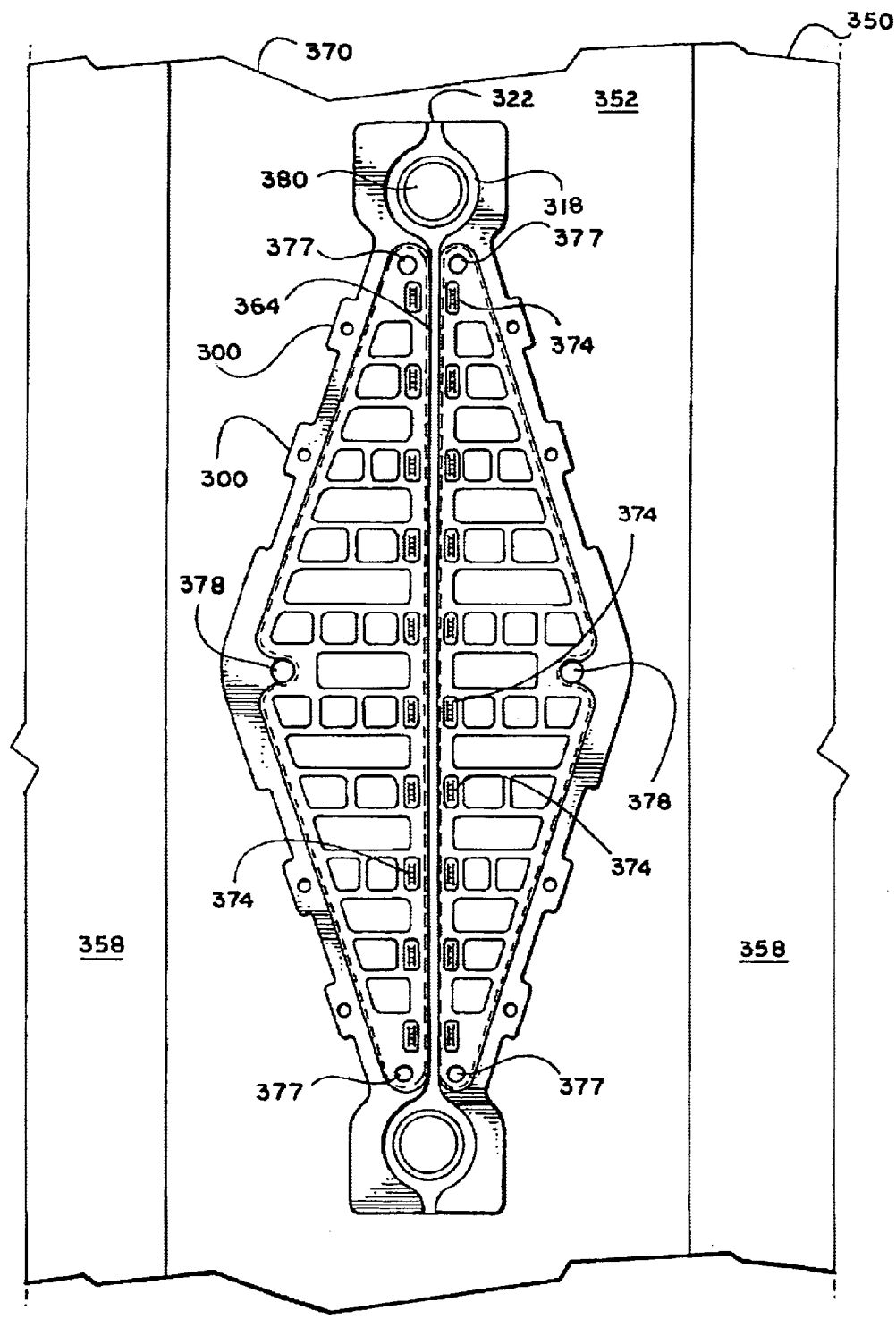
Fig_19

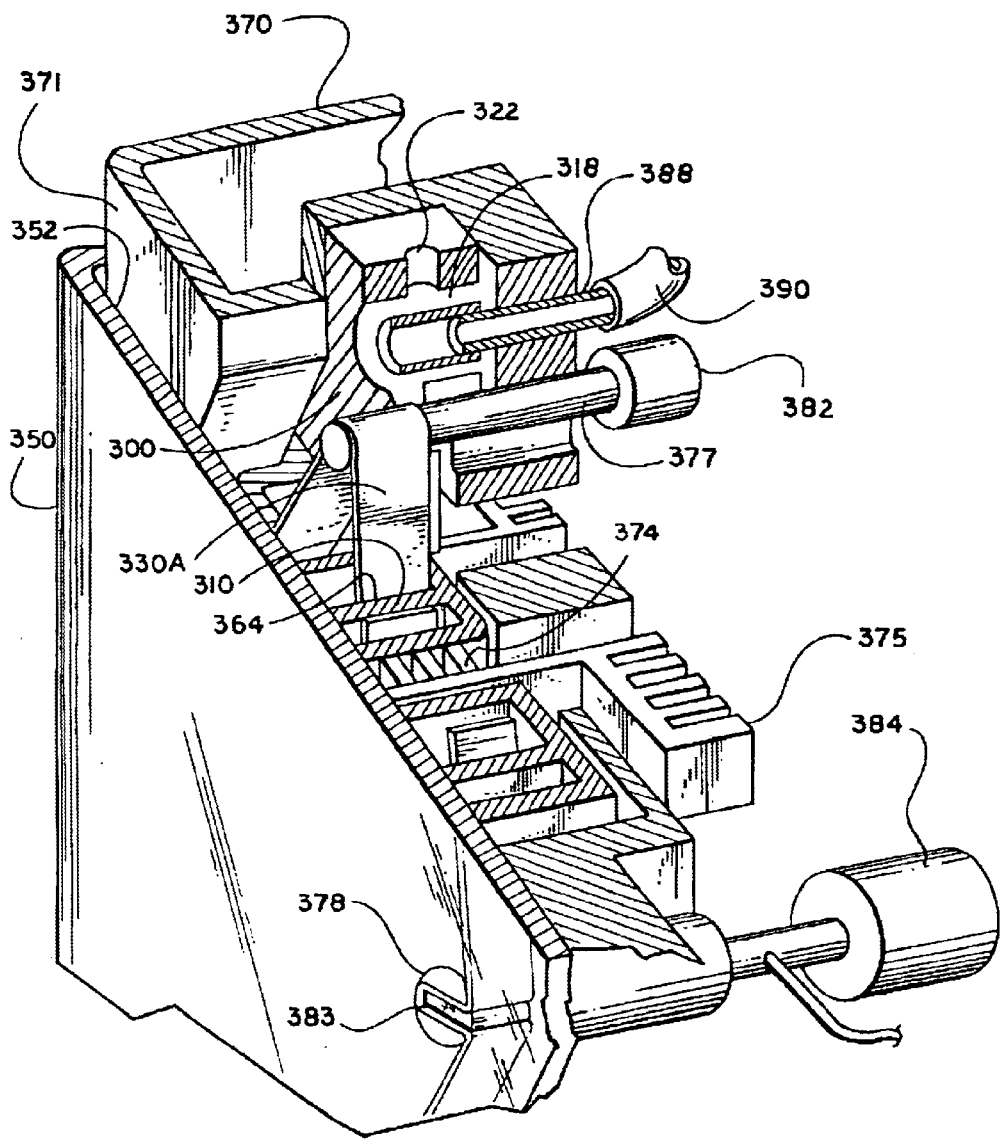
Fig_20

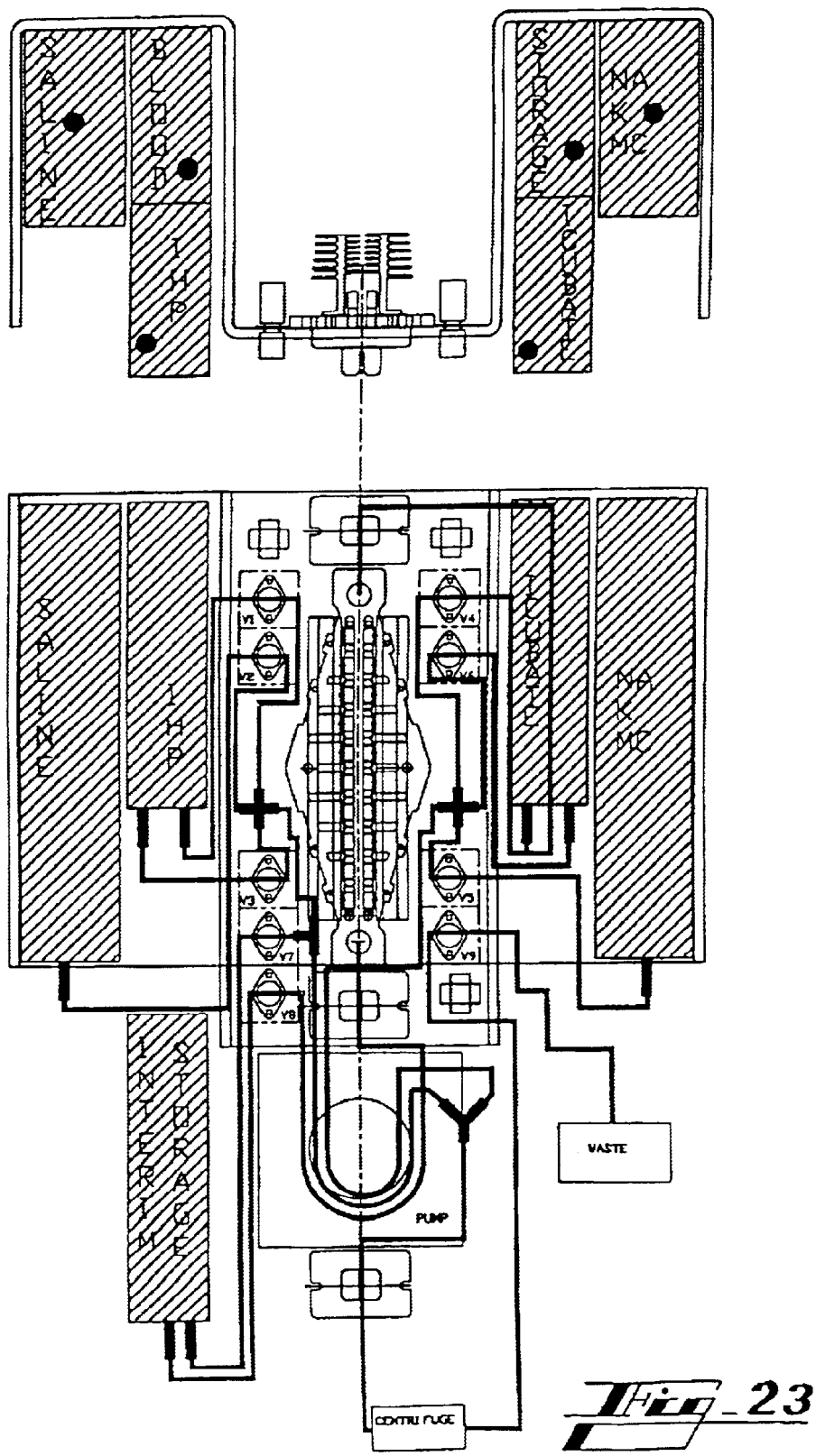
Fig_23

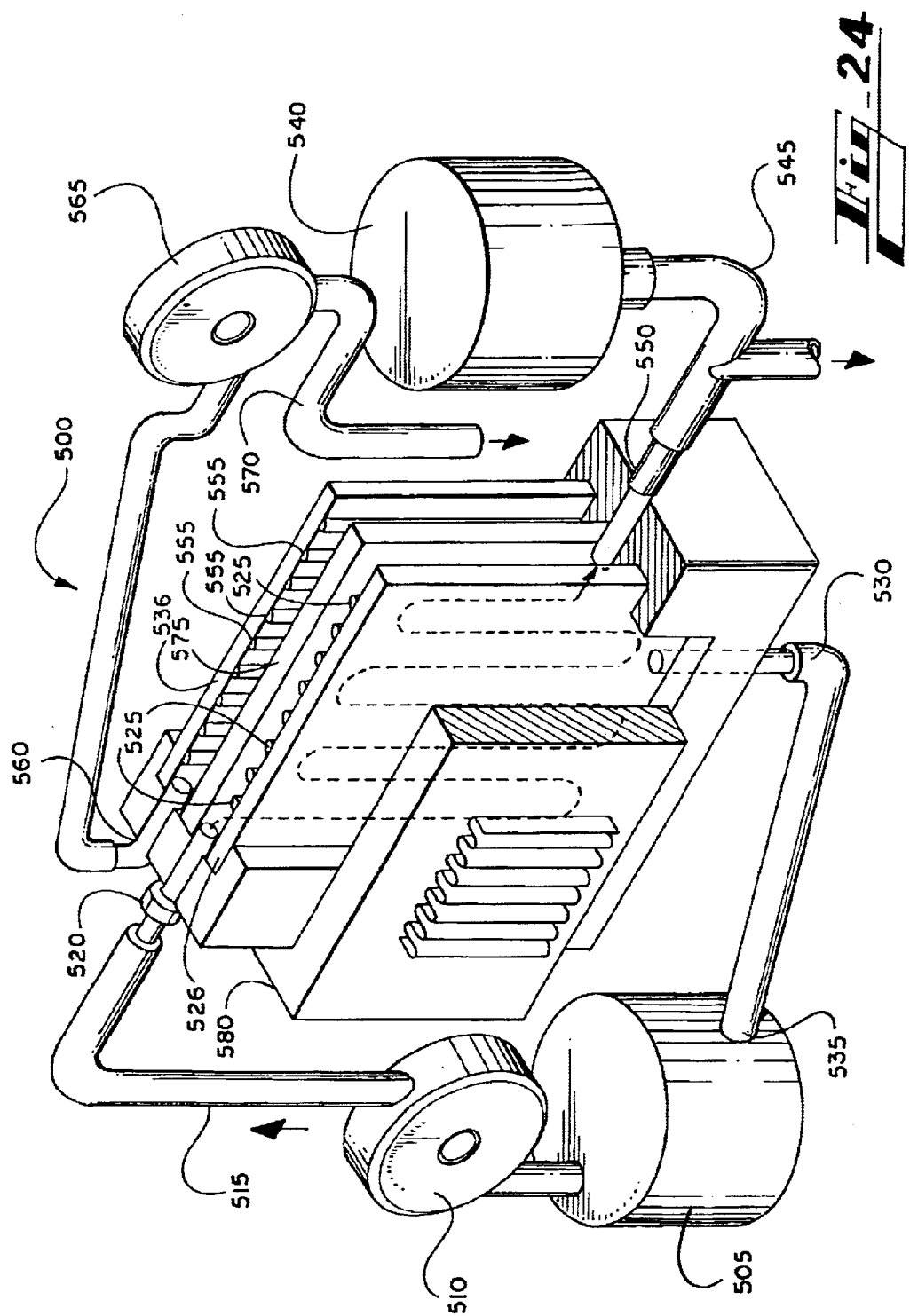

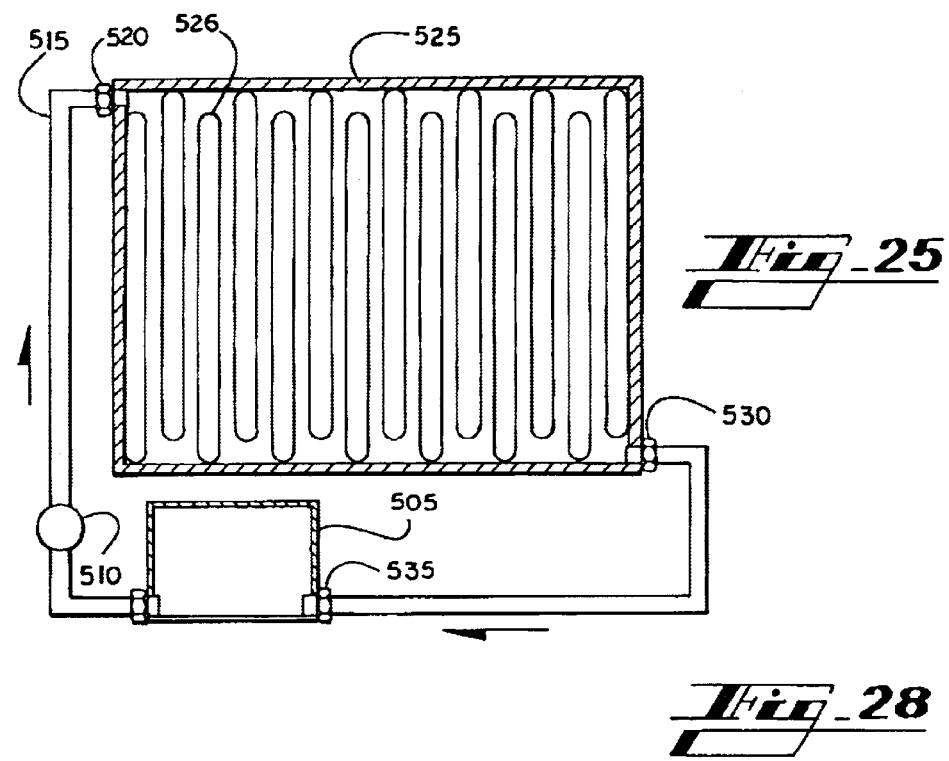
Fig_25
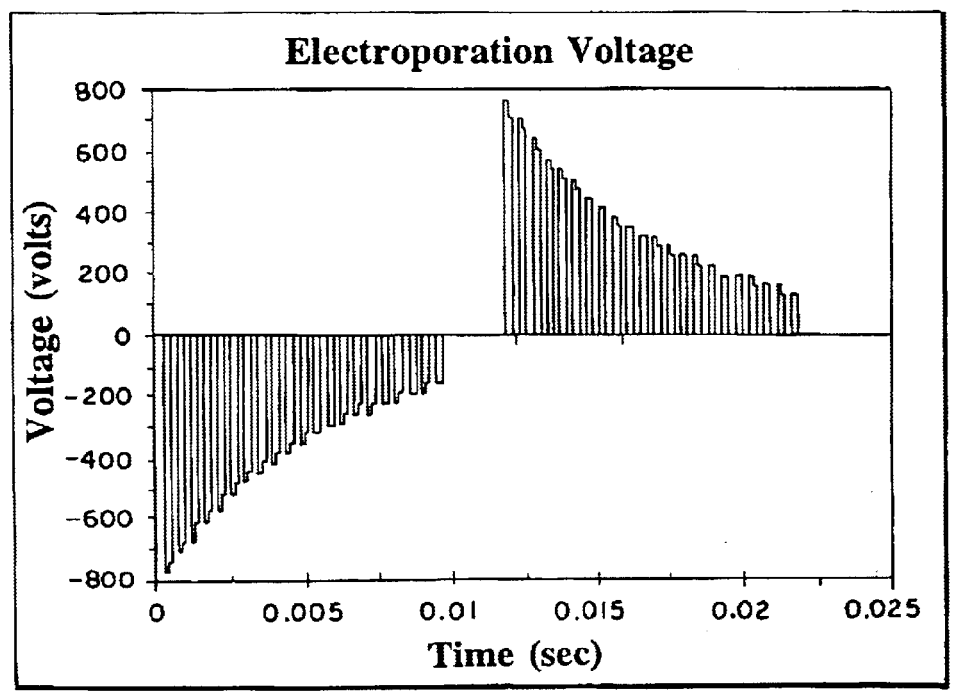
Fig_28

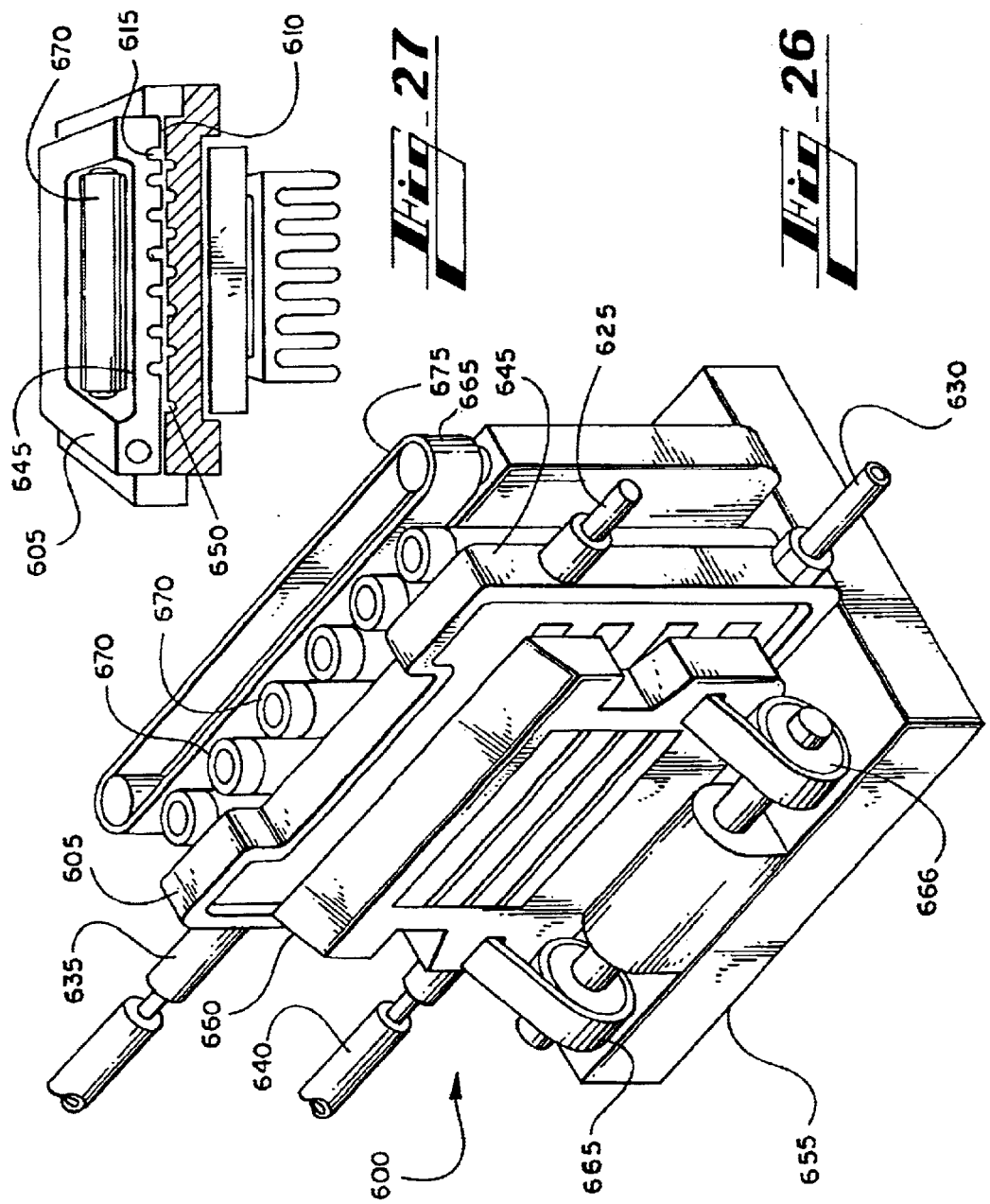

FLOW ELECTROPORATION CHAMBER AND METHOD

CROSS-REFERENCE TO RELATED APPLICATIONS

This application is a continuation application of U.S. patent application Ser. No. 09/397,303, filed Sep. 15, 1999 now abandoned, which is a continuation-in-part of U.S. patent application Ser. No. 08/627,843 (issued as U.S. Pat. No. 6,074.605) filed Mar. 11, 1996, which is a continuation-in-part of U.S. patent application Ser. No. 08/402,145 (issued as U.S. Pat. No. 5,720,921) filed Mar. 10, 1995 and a nonprovisional application of U.S. Provisional Patent Application, Serial No. 60/004,906, filed Oct. 6, 1995.

TECHNICAL FIELD

The present invention relates to methods and apparatus for the encapsulation of biologically-active substances in various cell populations. More particularly, the present invention relates to a method and apparatus for the encapsulation of allosteric effectors of hemoglobin in erythrocytes by electroporation to achieve therapeutically desirable changes in the physical characteristics of the intracellular hemoglobin.

BACKGROUND OF THE INVENTION

In the vascular system of an adult human being, blood has a volume of about 5 to 6 liters. Approximately one half of this volume is occupied by cells, including red blood cells (erythrocytes), white blood cells (leukocytes), and blood platelets. Red blood cells comprise the majority of the cellular components of blood. Plasma, the liquid portion of blood, is approximately 90 percent water and 10 percent various solutes. These solutes include plasma proteins, organic metabolites and waste products, and inorganic compounds.

The major function of red blood cells is to transport oxygen from the lungs to the tissues of the body, and transport carbon dioxide from the tissues to the lungs for removal. Very little oxygen is transported by the blood plasma because oxygen is only sparingly soluble in aqueous solutions. Most of the oxygen carried by the blood is transported by the hemoglobin of the erythrocytes. Erythrocytes in mammals do not contain nuclei, mitochondria or any other intracellular organelles, and they do not use oxygen in their own metabolism. Red blood cells contain about 35 percent by weight hemoglobin, which is responsible for binding and transporting oxygen.

Hemoglobin is a protein having a molecular weight of approximately 64,500 daltons. It contains four polypeptide chains and four heme prosthetic groups in which iron atoms are bound in the ferrous state. Normal globin, the protein portion of the hemoglobin molecule, consists of two $\alpha$ chains and two $\beta$ chains and is therefore characterized as a tetramer. Each of the four chains has a characteristic tertiary structure in which the chain is folded. The four polypeptide chains fit together in an approximately tetrahedral arrangement, to constitute the characteristic quaternary structure of hemoglobin. There is one heme group bound to each polypeptide chain which can reversibly bind one molecule of molecular oxygen. When hemoglobin combines with oxygen, oxyhemoglobin is formed. When oxygen is released, the oxyhemoglobin is reduced to deoxyhemoglobin.

Hemoglobin is found in erythrocytes where it is responsible for binding oxygen in the lung and transporting the bound oxygen throughout the body where it is used in aerobic metabolic pathways. Each chain or subunit of a hemoglobin tetramer has a heme prosthetic group identical to that described for myoglobin. The common peptide subunits are designated $\alpha$, $\beta$, $\gamma$ and $\Delta$ which are arranged into the most commonly occurring functional hemoglobins.

Although the secondary and tertiary structure of various hemoglobin subunits are similar, reflecting extensive homology in amino acid composition, the variations in amino acid composition that do exist impart marked differences in hemoglobin's oxygen carrying properties. In addition, the quaternary structure of hemoglobin leads to physiologically important allosteric interactions between the subunits, a property lacking in monomeric myoglobin which is otherwise very similar to the $\alpha$-subunit of hemoglobin.

Comparison of the oxygen binding properties of myoglobin and hemoglobin illustrate the allosteric properties of hemoglobin that results from its quaternary structure and differentiate hemoglobin's oxygen binding properties from that of myoglobin. The curve of oxygen binding to hemoglobin is sigmoidal typical of allosteric proteins in which the substrate, in this case oxygen, is a positive homotropic effector. When oxygen binds to the first subunit of deoxyhemoglobin it increases the affinity of the remaining subunits for oxygen. As additional oxygen is bound to the second and third subunits oxygen binding is further incrementally, strengthened, so that at the oxygen tension in lung alveoli, hemoglobin is fully saturated with oxygen. As oxyhemoglobin circulates to deoxygenated tissue, oxygen is incrementally unloaded and the affinity of hemoglobin for oxygen is reduced. Thus at the lowest oxygen tensions found in very active tissues the binding affinity of hemoglobin for oxygen is very low allowing maximal delivery of oxygen to the tissue. In contrast the oxygen binding curve for myoglobin is hyperbolic in character indicating the absence of allosteric interactions in this process. When the affinity for oxygen is increased, the sigmoidal curve is shifted to the right. This shift of the curve is commonly known as a "right shift".

The allosteric oxygen binding properties of hemoglobin arise directly from the interaction of oxygen with the iron atom of the heme prosthetic groups and the resultant effects of these interactions on the quaternary structure of the protein. When oxygen binds to an iron atom of deoxyhemoglobin it pulls the iron atom into the plane of the heme. Since the iron is also bound to histidine F8, this residue is also pulled toward the plane of the heme ring. The conformational change at histidine F8 is transmitted throughout the peptide backbone resulting in a significant change in tertiary structure of the entire subunit. Conformational changes at the subunit surface lead to a new set of binding interactions between adjacent subunits. The latter changes include disruption of salt bridges and formation of new hydrogen bonds and new hydrophobic interactions, all of which contribute to the new quaternary structure.

The latter changes in subunit interaction are transmitted, from the surface, to the heme binding pocket of a second deoxy subunit and result in easier access of oxygen to the iron atom of the second heme and thus a greater affinity of the hemoglobin molecule for a second oxygen molecule. The tertiary configuration of low affinity, deoxygenated hemoglobin (Hb) is known as the taut (T) state. Conversely, the quaternary structure of the fully oxygenated high affinity form of hemoglobin (HbO$_2$) is known as the relaxed (R) state.

Delivery of oxygen to tissues depends upon a number of factors including, but not limited to, the volume of blood flow, the number of red blood cells, the concentration of hemoglobin in the red blood cells, the oxygen affinity of the hemoglobin and, in certain species, on the molar ratio of intraerythrocytic hemoglobins with high and low oxygen affinity. The oxygen affinity of hemoglobin depends on four factors as well, namely: (1) the partial pressure of oxygen; (2) the pH; (3) the concentration of the allosteric effector 2,3-diphosphoglycerate (DPG) in the hemoglobin; and (4) the concentration of carbon dioxide. In the lungs, at an oxygen partial pressure of 100 mm Hg, approximately 98% of circulating hemoglobin is saturated with oxygen. This represents the total oxygen transport capacity of the blood. When fully oxygenated, 100 ml of whole mammalian blood can carry about 21 ml of gaseous oxygen.

The effect of the partial pressure of oxygen and the pH on the ability of hemoglobin to bind oxygen is best illustrated by examination of the oxygen saturation curve of hemoglobin. An oxygen saturation curve plots the percentage of total oxygen-binding sites of a hemoglobin molecule that are occupied by oxygen molecules when solutions of the hemoglobin molecule are in equilibrium with different partial pressures of oxygen in the gas phase.

As stated above, the oxygen saturation curve for hemoglobin is sigmoid. Thus, binding the first molecule of oxygen increases the affinity of the remaining hemoglobin for binding additional oxygen molecules. As the partial pressure of oxygen is increased, a plateau is approached at which each of the hemoglobin molecules is saturated and contains the upper limit of four molecules of oxygen.

The reversible binding of oxygen by hemoglobin is accompanied by the release of protons, according to the equation:

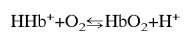

Thus, an increase in the pH will pull the equilibrium to the right and cause hemoglobin to bind more oxygen at a given partial pressure. A decrease in the pH will decrease the amount of oxygen bound.

In the lungs, the partial pressure of oxygen in the air spaces is approximately 90 to 100 mm Hg and the pH is also high relative to normal blood pH (up to 7.6). Therefore, hemoglobin will tend to become almost maximally saturated with oxygen in the lungs. At that pressure and pH, hemoglobin is approximately 98 percent saturated with oxygen. On the other hand, in the capillaries in the interior of the peripheral tissues, the partial pressure of oxygen is only about 25 to 40 mm Hg and the pH is also relatively low (about 7.2 to 7.3). Because muscle cells use oxygen at a high rate thereby lowering the local concentration of oxygen, the release of some of the bound oxygen to the tissue is favored. As the blood passes through the capillaries in the muscles, oxygen will be released from the nearly saturated hemoglobin in the red blood cells into the blood plasma and thence into the muscle cells. Hemoglobin will release about a third of its bound oxygen as it passes through the muscle capillaries, so that when it leaves the muscle, it will be only about 64 percent saturated. In general, the hemoglobin in the venous blood leaving the tissue cycles between about 65 and 97 percent saturation with oxygen in its repeated circuits between the lungs and the peripheral tissues. Thus, oxygen partial pressure and pH function together to effect the release of oxygen by hemoglobin A third important factor in regulating the degree of oxygenation of hemoglobin is the allosteric effector 2,3-diphosphoglycerate (DPG). DPG is the normal physiological effector of hemoglobin in mammalian erythrocytes. DPG regulates the oxygen-binding affinity of hemoglobin in the red blood cells in relationship to the oxygen partial pressure in the lungs. In general, the higher the concentration of DPG in the cell, the lower the affinity of hemoglobin for oxygen.

When the delivery of oxygen to the tissues is chronically reduced, the concentration of DPG in the erythrocytes is increased in normal individuals. For example, at high altitudes the partial pressure of oxygen is significantly less. Correspondingly, the partial pressure of oxygen in the tissues is less. Within a few hours after a normal human subject moves to a higher altitude, the DPG level in the red blood cells increases, causing more DPG to be bound and the oxygen affinity of the hemoglobin to decrease. Increases in the DPG level of red cells also occur in patients suffering from hypoxia. This adjustment allows the hemoglobin to release its bound oxygen more readily to the tissues to compensate for the decreased oxygenation of hemoglobin in the lungs. The reverse change occurs when people acclimated to high altitudes and descend to lower altitudes.

As normally isolated from blood, hemoglobin contains a considerable amount of DPG. When hemoglobin is "stripped" of its DPG, it shows a much higher affinity for oxygen. When DPG is increased, the oxygen binding affinity of hemoglobin decreases. A physiologic allosteric effector such as DPG is therefore essential for the normal release of oxygen from hemoglobin in the tissues.

While DPG is the normal physiologic effector of hemoglobin in mammalian red blood cells, phosphorylated inositols are found to play a similar role in the erythrocytes of some birds and reptiles. Although IHP is unable to pass through the mammalian erythrocyte membrane, it is capable of combining with hemoglobin of mammalian red blood cells at the binding site of DPG to modify the allosteric conformation of hemoglobin, the effect of which is to reduce the affinity of hemoglobin for oxygen. For example, DPG can be replaced by inositol hexaphosphate (IHP), which is even more potent than DPG in reducing the oxygen affinity of hemoglobin. IHP has a 1000-fold higher affinity to hemoglobin than DPG (R. E. Benesch et al., *Biochemistry*, Vol. 16, pages 2594–2597 (1977)) and increases the $P_{50}$ of hemoglobin up to values of 96.4 mm Hg at pH 7.4, and 37 degrees C (*J. Biol. Chem.*, Vol. 250, pages 7093–7098 (1975)).

The oxygen release capacity of mammalian red blood cells can be enhanced by introducing certain allosteric effectors of hemoglobin into erythrocytes, thereby decreasing the affinity of hemoglobin for oxygen and improving the oxygen economy of the blood. This phenomenon suggests various medical applications for treating individuals who are experiencing lowered oxygenation of their tissues due to the inadequate function of their lungs or circulatory system.

Because of the potential medical benefits to be achieved from the use of these modified erythrocytes, various techniques have been developed in the prior art to enable the encapsulation of allosteric effectors of hemoglobin in erythrocytes. Accordingly, numerous devices have been designed to assist or simplify the encapsulation procedure. The encapsulation methods known in the art include osmotic pulse (swelling) and reconstitution of cells, controlled lysis and resealing, incorporation of liposomes, and electroporation. Current methods of electroporation make the procedure commercially impractical on a scale suitable for commercial use.

The following references describe the incorporation of polyphosphates into red blood cells by the interaction of liposomes loaded with IHP: Gersonde, et al., "Modification of the Oxygen Affinity of Intracellular Haemoglobin by Incorporation of Polyphosphates into Intact Red Blood Cells and Enhanced O2 Release in the Capillary System", *Biblthca. Haemat.*, No. 46, pp. 81–92 (1980); Gersonde, et al., "Enhancement of the O2 Release Capacity and of the Bohr-Effect of Human Red Blood Cells after Incorporation of Inositol Hexaphosphate by Fusion with Effector-Containing Lipid Vesicles", *Origins of Cooperative Binding of Hemoglobin*, (1982); and Weiner, "Right Shifting of Hb—$O_2$ Dissociation in Viable Red Cells by Liposomal Technique," *Biology of the Cell*, Vol. 47, (1983).

Additionally, U.S. Pat. Nos. 4,192,869, 4,321,259, and 4,473,563 to Nicolau et al. describe a method whereby fluid-charged lipid vesicles are fused with erythrocyte membranes, depositing their contents into the red blood cells. In this manner, it is possible to transport allosteric effectors such as inositol hexaphosphate into erythrocytes, where, due to its much higher binding constant IHP replaces DPG at its binding site in hemoglobin.

In accordance with the liposome technique, IHP is dissolved in a phosphate buffer until the solution is saturated and a mixture of lipid vesicles is suspended in the solution. The suspension is then subjected to ultrasonic treatment or an injection process, and then centrifuged. The upper suspension contains small lipid vesicles containing IHP, which are then collected. Erythrocytes are added to the collected suspension and incubated, during which time the lipid vesicles containing IHP fuse with the cell membranes of the erythrocytes, thereby depositing their contents into the interior of the erythrocyte. The modified erythrocytes are then washed and added to plasma to complete the product.

The drawbacks associated with the liposomal technique include poor reproducibility of the IHP concentrations incorporated in the red blood cells and significant hemolysis of the red blood cells following treatment. Additionally, commercialization is not practical because the procedure is tedious and complicated.

In an attempt to solve the drawbacks associated with the liposomal technique, a method of lysing and the resealing red blood cells was developed. This method is described in the following publication: Nicolau, et al., "Incorporation of Allosteric Effectors of Hemoglobin in Red Blood Cells. Physiologic Effects," *Biblthca. Haemat.*, No. 51, pp. 92–107, (1985). Related U.S. Pat. Nos. 4,752,586 and 4,652,449 to Ropars et al. also describe a procedure of encapsulating substances having biological activity in human or animal erythrocytes by controlled lysis and resealing of the erythrocytes, which avoids the RBC-liposome interactions.

The technique is best characterized as a continuous flow dialysis system which functions in a manner similar to the osmotic pulse technique. Specifically, the primary compartment of at least one dialysis element is continuously supplied with an aqueous suspension of erythrocytes while the secondary compartment of the dialysis element contains an aqueous solution which is hypotonic with respect to the erythrocyte suspension. The hypotonic solution causes the erythrocytes to lyse. The erythrocyte lysate is then contacted with the biologically active substance to be incorporated into the erythrocyte. To reseal the membranes of the erythrocytes, the osmotic and/or oncotic pressure of the erythrocyte lysate is increased and the suspension of resealed erythrocytes is recovered.

In related U.S. Pat. Nos. 4,874,690 and 5,043,261 to Goodrich et al. a related technique involving lyophilization and reconstitution of red blood cells is disclosed. As part of the process of reconstituting the red blood cells, the addition of various polyanions, including inositol hexaphosphate, is described. Treatment of the red blood cells according to the process disclosed results in a cell with unaffected activity. Presumably, the IHP is incorporated into the cell during the reconstitution process, thereby maintaining the activity of the hemoglobin.

In U.S. Pat. Nos. 4,478,824 and 4,931,276 to Franco et al. a second related method and apparatus is described for introducing effective agents, including inositol hexaphosphate, into mammalian red blood cells by effectively lysing and resealing the cells. The procedure is described as the "osmotic pulse technique." In practicing the osmotic pulse technique, a supply of packed red blood cells is suspended and incubated in a solution containing a compound which readily diffuses into and out of the cells, the concentration of the compound being sufficient to cause diffusion thereof into the cells so that the contents of the cells become hypertonic. Next, a trans-membrane ionic gradient is created by diluting the solution containing the hypertonic cells with an essentially isotonic aqueous medium in the presence of at least one desired agent to be introduced, thereby causing diffusion of water into the cells with a consequent swelling and an increase in permeability of the outer membranes of the cells. This "osmotic pulse" resulting in the diffusion of water into the cells and consequent swelling of the cells, increases the permeability of the outer cell membrane to the desired agent The increase in permeability of the membrane is maintained for a period of time sufficient only to permit transport of least one agent into the cells and diffusion of the compound out of the cells.

Polyanions which may be used in practicing the osmotic pulse technique include pyrophosphate, tripolyphosphate, phosphorylated inositols, 2,3-diphosphoglycerate (DPG), adenosine triphosphate, heparin, and polycarboxylic acids which are water-soluble, and non-disruptive to the lipid outer bilayer membranes of red blood cells.

The osmotic pulse technique has several shortcomings including the fact that the technique is tedious, complicated and unsuited to automation. In addition, the results are typically unpredictable and unreliable. For these reasons, the osmotic pulse technique has had little commercial success.

Another method for encapsulating various biologically-active substances in erythrocytes is electroporation. Electroporation has been used for encapsulation of foreign molecules in different cell types including IHP red blood cells as described in Mouneimne, et al., "Stable rightward shifts of the oxyhemoglobin dissociation curve induced by encapsulation of inositol hexaphosphate in red blood cells using electroporation," FEBS, Vol. 275, No. 1, 2, pp. 117–120 (1990).

The process of electroporation involves the formation of pores in the cell membranes, or in any vesicles, by the application of electric field pulses across a liquid cell suspension containing the cells or vesicles. During the poration process, cells are suspended in a liquid media and then subjected to an electric field pulse. The medium may be electrolyte, non-electrolyte, or a mixture of electrolytes and non-electrolytes. The strength of the electric field applied to the suspension and the length of the pulse (the time that the electric field is applied to a cell suspension) varies according to the cell type. To create a pore in a cell's outer membrane, the electric field must be applied for such a length of time and at such a voltage as to create a set potential across the cell membrane for a period of time long enough to create a pore.

Four phenomenon appear to play a role in the process of electroporation. The first is the phenomenon of dielectric breakdown. Dielectric breakdown refers to the ability of a high electric field to create a small pore or hole in a cell membrane. Once a pore is created, a cell can be loaded with a biologically-active substances. The second phenomenon is the dielectric bunching effect, which refers to the mutual self attraction produced by the placement of vesicles in a uniform electric field. The third phenomenon is that of vesicle fusion. Vesicle fusion refers to the tendency of membranes of biological vesicles, which have had pores formed by dielectric breakdowns, to couple together at their mutual dialectic breakdown sites when they are in close proximity. The fourth phenomenon is the tendency of cells to line up along one of their axis in the presence of high frequency electric fields. Thus, electroporation relates to the use in vesicle rotational prealignment, vesicle bunching and dialectic constant or vesicles for the purpose of loading and unloading the cell vesicle.

Electroporation has been used effectively to incorporate allosteric effectors of hemoglobin in erythrocytes. In the article by Mouneimne et al., FEBS, Vol. 275, No. 1, 2, pages 11–120 (1990), Mouneimne and his colleagues reported that right shifts of the hemoglobin-oxygen dissociation in treated erythrocytes having incorporated IHP can be achieved. Measurements at 24 and 48 hours after loading with IHP showed a stable $P_{50}$ value indicating that resealing of the erythrocytes was permanent. Furthermore, it was shown that red blood cells loaded with inositol hexaphosphate have a normal half life of eleven days. However, the results obtained by Mouneimne and his colleagues indicate that approximately 20% of the retransfused cells were lost within the first 24 hours of transfusion.

The electroporation methods disclosed in the prior art are not suitable for processing large volumes of sample, nor use of a high or repetitive electric charge. In addition, the stability of the $P_{50}$ right shift as well as the stability of the red blood cells has not proved adequate for clinical use. Furthermore, the methods are not suitable for use in a continuous or "flow" electroporation chamber. Available electroporation chambers are designed for static use only. Namely, processing of samples in small batches. A typical format for a "static" chamber comprises a small glass cuvette, with very limited space for particle motion. Continuous use of a "static" chamber results in over heating of the chamber and increased cell lysis. Furthermore, the existing technology is unable to incorporate a sufficient quantity of IHP in a sufficient percentage of the cells being processed to dramatically change the oxygen carrying capacity of the blood. In addition, the prior art methods require elaborate equipment and are not suited for loading red blood cells of a patient at the point of care. Thus, the procedure is time consuming and not suitable for use on a commercial scale.

What is needed is a simple, efficient and rapid method for encapsulating biologically-active substances in erythrocytes in sufficient volume while preserving the integrity and biologic function of the cells. The potential therapeutic applications of biologically altered blood cells suggests the need for simpler, and more effective and complete methods of encapsulation of biologically-active substances, including allosteric effectors of hemoglobin in intact erythrocytes.

There are numerous clinical conditions that would benefit from treatments that would increase tissue delivery of oxygen bound to hemoglobin. For example, the leading cause of death in the United States today is cardiovascular disease. The acute symptoms and pathology of many cardiovascular diseases, including congestive heart failure, ischemia, myocardial infarction, stroke, intermittent claudication, and sickle cell anemia, result from an insufficient supply of oxygen in fluids that bathe the tissues. Likewise, the acute loss of blood following hemorrhage, traumatic injury, or surgery results in decreased oxygen supply to vital organs. Without oxygen, tissues at sites distal to the heart, and even the heart itself, cannot produce enough energy to sustain their normal functions. The result of oxygen deprivation is tissue death and organ failure. Another area that would benefit from treatments that would increase tissue delivery of oxygen bound to hemoglobin is racing animals, athletes, etc.

Another area is in treating diseases such as adult respiratory distress syndrome because administration of blood that is capable of increased delivery of oxygen to the peripheral tissues will ease the pressure of loading hemoglobin in the lungs.

Although the attention of the American public has long been focused on the preventive measures required to alleviate heart disease, such as exercise, appropriate dietary habits, and moderation in alcohol consumption, deaths continue to occur at an alarming rate. Since death results from oxygen deprivation, which in turn results in tissue destruction and/or organ dysfunction, one approach to alleviate the life-threatening consequences of cardiovascular disease is to increase oxygenation of tissues during acute stress. The same approach is also appropriate for persons suffering from blood loss or chronic hypoxic disorders, such as congestive heart failure.

Another condition which could benefit from an increase in the delivery of oxygen to the tissues is anemia. A significant portion of hospital patients experience anemia or a low "crit" caused by an insufficient quantity of red blood cells or hemoglobin in their blood. This leads to inadequate oxygenation of their tissues and subsequent complications. Typically, a physician believes that he or she can temporarily correct this condition by transfusing the patient with units of packed red blood cells.

Enhanced blood oxygenation may also reduce the number of heterologous transfusions and allow use of autologous transfusions in more cases. The current method for treatment of anemia or replacement of blood loss is transfusion of whole human blood. It is estimated that three to four million patients receive transfusions in the U.S. each year for surgical or medical needs. In situations where there is more time or where the religious beliefs of the patient forbid the use of heterologous blood for transfusions, it is advantageous to completely avoid the use of donor or heterologous blood and instead use autologous blood.

Often the amount of blood which can be drawn and stored prior to surgery limits the use of autologous blood. Typically, a surgical patient does not have enough time to donate a sufficient quantity of blood prior to surgery. A surgeon would like to have several units of blood available. As each unit requires a period of several weeks between donations and can not be done less than two weeks prior to surgery, it is often impossible to sequester an adequate supply of blood. By processing autologous blood with IHP, less blood is required and it becomes possible to completely avoid the transfusion of heterologous blood.

As IHP-treated red cells transport 2–3 times as much oxygen as untreated red cells, in many cases, a physician will need to transfuse fewer units of IHP-treaded red cells. This exposes the patient to less heterologous blood, decreases the extent of exposure to viral diseases from blood donors and minimizes immune function disturbances secondary to transfusions. The ability to infuse more efficient red blood cells is also advantageous when the patient's blood volume is excessive. In other more severe cases, where oxygen transport is failing, the ability to rapidly improve a patient's tissue oxygenation is life saving.

Although it is evident that methods of enhancing oxygen delivery to tissues have potential medical applications, currently there are no methods clinically available for increasing tissue delivery of oxygen bound to hemoglobin. Transient, 6 to 12 hour elevations of oxygen deposition have been described in experimental animals using either DPG or molecules that are precursors of DPG. The natural regulation of DPG synthesis in vivo and its relatively short biological half-life, however, limit the DPG concentration and the duration of increased tissue $PO_2$, and thus limit its therapeutic usefulness.

What is needed is a simple, efficient and rapid method for encapsulating biologically-active substances, such as IHP, in erythrocytes without damaging the erythrocytes beyond their ability to produce a clinical effect. An important requirement for any system of introducing IHP into red blood cells is that the right shift of the sigmoidal oxygen binding curve be substantially stable and the red blood cell must be substantially similar to untreated red blood cells.

SUMMARY OF THE INVENTION

The present invention relates to a method and apparatus for the encapsulation of biologically-active substances in various cell populations. More specifically, the present invention provides an electroporation chamber that may form part of an automated, self-contained, flow apparatus for encapsulating compounds or compositions, such as inositol hexaphosphate, in red blood cells, thereby reducing the affinity of the hemoglobin for oxygen and enhancing the delivery of oxygen by red blood cells to tissues. Encapsulation is preferably achieved by electroporation; however, it is contemplated that other methods of encapsulation may be used in practicing the present invention. The method and apparatus, including the electroporation chamber, of the present invention, is equally suited to the encapsulation of a variety of biologically-active substances in various cell populations.

The apparatus and method of the present invention is suited to the incorporation of a variety of biologically-active substances in cells and lipid vesicles. The method, apparatus and chamber of the present invention may be used for introducing a compound or biologically-active substance into a vesicle whether that vesicle is engineered or naturally occurring.

In one embodiment of the present invention, substances or drugs can be introduced into cells or fragments of cells such as platelets. For example, thrombus dissolving substances such as tissue plasminogen activator or streptokinase and the like can be introduced into a population of platelets. These platelets loaded with the thrombus dissolving substances can be then introduced into a patient who is suffering from a thrombus blocking a blood vessel. The platelet containing the thrombus dissolving substance will then migrate to the site of the thrombus and attach itself to the thrombus. Because the treated platelets contain active thrombus dissolving enzymes, the thrombus is then dissolved. The thrombus dissolving substances can be introduced into the platelets by a variety of methods with the most preferable method being according to the apparatus of the present invention.

The apparatus, method, and chamber of the present invention may be used to introduce IHP into erythrocytes. The encapsulation of inositol hexaphosphate in red blood cells by electroporation according to the present invention results in a significant decrease in the hemoglobin affinity for oxygen without substantially affecting the life span, ATP levels, K+ levels, or normal rheological competence of the cells. In addition, the Bohr effect is not altered except to shift the $O_2$ binding curve to the right. Lowering the oxygen affinity of the erythrocytes increases the capacity of erythrocytes to dissociate the bound oxygen and thereby improves the oxygen supply to the tissues. Enhancement of the oxygen-release capacity of erythrocytes brings about significant physiological effects such as a reduction in cardiac output, an increase in the arteriovenous differences, and improved tissue oxygenation.

The modified erythrocytes prepared in accordance with the present invention, having improved oxygen release capacities, may find their use in situations such as those illustrated below:

1. Under conditions of low oxygen-partial pressure, such as at high altitudes;
2. When the oxygen exchange surface of the lung is reduced, such as occurs in emphysema and adult respiratory distress syndrome;
3. When there is an increased resistance to oxygen diffusion in the lung, such as occurs in pneumonia or asthma;
4. When there is a decrease in the oxygen-transport capacity of erythrocytes, such as occurs with erythropenia or anemia, or when an arteriovenous shunt is used;
5. To treat blood circulation disturbances, such as arteriosclerosis, thromboembolic processes, organ infarct, congestive heart failure, cardiac insufficiency or ischemia;
6. To treat conditions of high, oxygen affinity of hemoglobin, such as hemoglobin mutations, chemical modifications of N-terminal amino acids in the hemoglobin-chains, or enzyme defects in erythrocytes;
7. To accelerate detoxification processes by improving oxygen supply;
8. To decrease the oxygen affinity of conserved blood; or
9. To improve the efficacy of various cancer treatments;
10. To enhance the athletic performance of humans or animals.

According to the method and apparatus of the present invention, it is possible to produce modified erythrocytes which contribute to an improved oxygen economy of the blood. These modified erythrocytes are obtained by incorporation of allosteric effectors, such as IHP, by electroporation of the erythrocyte membranes.

The incorporation of the biologically-active substances into the cells in accordance with the method of the present invention, including the encapsulation of allosteric effectors of hemoglobin into erythrocytes, is conducted extracorporally via an automated, flow electroporation apparatus. Briefly, a cell suspension is introduced into the separation and wash bowl chamber of the flow encapsulation apparatus. The cells are separated from the suspension, washed and resuspended in a solution of the biologically-active substance to be introduced into the cell. This suspension is introduced into the electroporation chamber and then incubated. Following electroporation and incubation, the cells are washed and separated. A contamination check is optionally conducted to confirm that all unencapsulated biologically-active substance has been removed. Then, the cells are prepared for storage or reintroduction into a patient.

In accordance with the present invention and with reference to the preferred embodiment, blood is drawn from a patient, the erythrocytes are separated from the drawn blood, the erythrocytes are modified by the incorporation of allosteric effectors and the modified erythrocytes and blood plasma is reconstituted. In this manner, it is possible to prepare and store blood containing IHP-modified erythrocytes.

The apparatus of the present invention provides an improved method for the encapsulation of biologically-active substances in cells including an apparatus which is self-contained and therefore sterile, an apparatus which can process large volumes of cells within a shortened time period, an apparatus having improved contamination detection, cooling and incubation elements, an apparatus that is entirely automated and which does not require the active control of a technician once a sample is introduced into the apparatus.

Another embodiment of the present invention is a preparation of red blood cells that has a stable right shifted oxygen dissociation curve. The phrase "stable right shifted blood" as used herein means that the right shifted oxygenation curve remains higher than untreated red blood cells over the same period of time. Untreated freshly drawn red blood cells will have a $P_{50}$ of approximately 27 mm Hg. This value decreases over time as it is stored in the blood bank at 2–8° C. due to the loss of the allosteric effector 2,3, diphosphoglycerate. After several days in storage the $P_{50}$ drops to around 22–25 mm Hg. After 1 to 2 weeks the value can drop to around 18–20 mm Hg. It is contemplated as part of the present invention a preparation of isolated red blood cells that have a $P_{50}$ greater than approximately 30 mm Hg. These red blood cells have a stable $P_{50}$ that remains substantially the same over the storage life of the red blood cell or the $P_{50}$ remains substantially above the $P_{50}$ of untreated blood over a period of time. Thus, one embodiment of the present invention is an isolated preparation of red blood cells that can be stored under normal blood bank conditions, e.g., 2–8° C., and has a substantially stable $P_{50}$ of greater than approximately 30 mm Hg, more desirably greater than approximately 35 mm Hg, even more desirably greater than approximately 40 mm Hg and most desirably greater than approximately 45 mm Hg.

It is further contemplated as part of the present invention that the red blood cells that have a substantially stable elevated $P_{50}$ have been treated with IHP so that the IHP passes through the red blood cell membrane so that it can bind allosterically to the DPG binding site of hemoglobin. The method of introducing the IHP into the interior of the red blood cell membrane can be by any method that will produce a substantially stable preparation of red blood cells with an elevated $P_{50}$. For example, the red blood cells can be treated as described herein by flow electroporation in the presence of IHP, or the red blood cells can be exposed to hypo or hyper osmotic agents, or to membrane solubilizing agents to allow a chemical such as IHP to pass through the red cell membrane so that the IHP molecule can bind allosterically to the DPG binding site thereby replacing the natural DPG in the allosteric binding site on the hemoglobin molecule.

In addition, the red blood cell preparation can be a population of normal, untreated red blood cells that naturally have an elevated $P_{50}$ level. A population of normal, untreated red blood cells that has an elevated $P_{50}$ level can be isolated by density gradient fractionation methods. (See e.g., Bourget et al., Adv. Exp. Med. Biol (1992))

The present invention includes a method of gene therapy including, but not limited to the introduction of DNA preparations into live cells. The DNA preparations preferably code for a desired protein and can optionally contain vectors that will facilitate the introduction of the DNA into the genetic mechanisms of the cell and thereby (1) increase the expression of the desired protein; (2) regulate the metabolism of a cell; (3) change the phenotype of a cell or (4) be used as a carrier inside the cell. These methods of adding vectors to naked DNA preparations are well know to those of ordinary skill in the art. The DNA that is introduced using the flow electroporation apparatus of the present invention can be naked DNA or can contain other agents to facilitate entry of the DNA into the cell.

Thus, it is an object of the present invention to provide an automated, continuous flow encapsulation apparatus.

It is a further object of the present invention to provide an automated, continuous flow electroporation apparatus.

It is a further object of the present invention to provide a continuous flow encapsulation apparatus which produces a homogenous population of loaded cells or vesicles.

It is another object of the present invention to provide a continuous flow electroporation device which produces a homogenous population of loaded cells or vesicles.

It is another object of the present invention to provide a sterile and nonpyrogenic method of encapsulating biologically-active substances in cells.

It is another object of the present invention to provided a method and apparatus which results in stable resealing of cells or vesicles following electroporation to minimize lysis of the modified cells or vesicles after electroporation.

It is another object of the present invention to provide a flow encapsulation apparatus which produces a modified cell population from which all exogenous non-encapsulated biologically-active substances have been removed.

It is another object of the present invention to provide an electroporation apparatus which produces a modified cell population from which all exogenous, non-encapsulated biologically-active substances have been removed.

It is another object of the present invention to provide a method and apparatus that allows continuous encapsulation of biologically-active substances in a population of cells or vesicles.

It is a further object of the present invention to provide a method and apparatus that achieves the above-defined objects, features, and advantages in a single cycle.

It is a further object of the present invention to provide a method and apparatus that is capable of introducing drugs and substances into platelets.

It is another object of the present invention to provide a continuous flow electroporation chamber.

It is another object of the present invention to provide an improved and more efficient method of encapsulating biologically active substances in cells than those methods currently available.

It is a further object of the present invention to provide a composition suitable for use in the treatment of conditions and/or disease states resulting from a lack of or decrease in oxygenation.

Other objects, features, and advantages of the present invention will become apparent upon reading the following detailed description of the preferred embodiment of the invention when taken in conjunction with the drawings and the appended claims.

BRIEF DESCRIPTION OF THE DRAWINGS

FIG. 3 is a top view of a first embodiment of the flow electroporation chamber with electrodes.

FIG. 4 is a top view of a first embodiment of the flow electroporation chamber without electrodes.

FIG. 5 is a side view of a first embodiment of the flow electroporation chamber.

FIG. 6 is an end view of a first embodiment of the flow electroporation chamber.

FIG. 9 is an exploded perspective view of a second embodiment of the flow electroporation chamber.

FIG. 10 is a perspective view of the flow electroporation chamber of FIG. 9 with the chamber being assembled.

FIG. 14 is a front elevation view of a support member of an electroporation chamber according to a third embodiment of the present invention.

FIG. 15 is a cross-sectional view of the support member of FIG. 14 taken along line 15—15 of FIG. 14.

FIG. 16 is an enlarged view of the section indicated by the circle 16 of FIG. 15.

FIG. 17 is an exploded perspective view of the electroporation chamber according to the third embodiment and support column to which the chamber is mounted.

FIG. 18 is a perspective view showing the electroporation chamber of FIG. 17 mounted to the support column.

FIG. 19 is a front elevation view of the electroporation chamber according to the third embodiment mounted to a support column.

FIG. 20 is a perspective cut-away view of the electroporation chamber and support column of FIG. 19.

FIG. 23 is a schematic diagram of a third embodiment of a continuous flow encapsulation apparatus.

FIG. 24 is a cutaway view of a cell washing apparatus.

FIG. 25 is a side view of the cell plate 526 showing the ridges defining the labyrinth and the tubing showing the recirculation of the cell suspension.

FIG. 26 is a cutaway view of a second embodiment of a cell washing apparatus.

FIG. 27 is a side cutaway view of the elastomeric chamber.

FIG. 28 is a graph showing representative electroporation voltage.

DETAILED DESCRIPTION OF THE INVENTION

Figure 1:
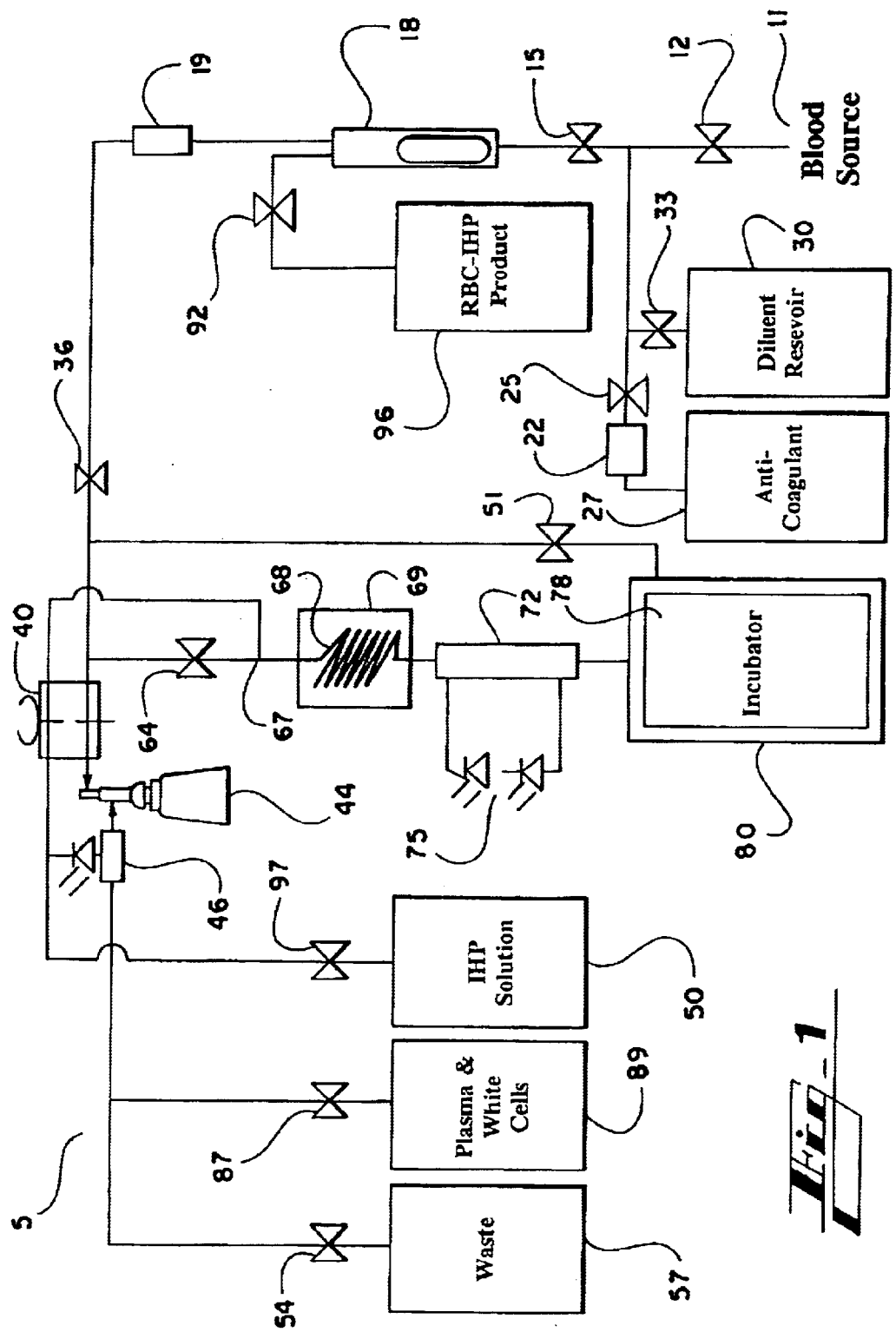
FIG. 1 is a schematic diagram of a first embodiment of a continuous flow encapsulation apparatus.

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference.

The present invention provides an automated, self-contained, flow apparatus for encapsulating allosteric compounds or compositions, such as inositol hexaphosphate (IHP), in cells or fragments of cells, including, but not limited to, red blood cells, white blood cell, platelets, stem cells, genetically engineered stem cells, or an expanded population of stem cells. In one embodiment, the apparatus of the present invention combines the features of a plasmaphoresis apparatus with those of a flow electroporation apparatus to form an automated, self-contained flow electroporation device. The present invention further comprises a new flow electroporation chamber that allows use of the chamber under flow rather than static conditions. It is contemplated that the method and apparatus, including the electroporation chamber of the present invention, may be used to encapsulate a variety of biologically-active substances in diverse cell populations.

In one embodiment, the present invention provides a population of modified cells having physical characteristics that make the cells particularly useful for treating conditions which demand or benefit from an increase in the delivery of oxygen to the tissues. In accordance with the method of the present invention, a homogenous population of IHP loaded red blood cells can be obtained with reduced contamination and a reduced propensity to lyse following encapsulation. The treated red blood cells exhibit normal life spans in circulation. Using the present invention, red blood cells of a patient in need of the treatment can be quickly loaded and returned to the patient's circulation.

Related International Application No. PCT/US94/03189, filed Mar. 23, 1994, which is a continuation-in-part of U.S. application Ser. No. 035,467, filed Mar. 23, 1993, is hereby incorporated by reference.

The method of operation of the apparatus of the present invention is described below with reference to the preferred use of the apparatus, i.e., the encapsulation of allosteric effectors of hemoglobin in red blood cells. Inositol hexaphosphate is the preferred allosteric effector to be used with the present invention. Other sugar phosphates, such as inositol pentaphosphate, inositol tetraphosphate, inositol triphosphate, inositol diphosphate, diphosphatidyl inositol diphosphate, and acetylated inositol phosphates, such as acetylated IHP, can also be used. Other suitable allosteric effectors include polyphosphates such as nucleotide triphosphates, nucleotide diphosphates, nucleotide monophosphates, and alcohol phosphate esters. In case of certain mutations of hemoglobin, e.g. "Zurich" hemoglobin, organic anions such as polycarboxylic acids can be used as allosteric effectors. Finally, it is possible to use inorganic anions such as hexacyano ferrate, phosphate or chloride as allosteric effectors.

Red blood cells that have been loaded with inositol hexaphosphate according to the present invention can be used to treat a wide variety of diseases and disease states. The IHP loaded red blood cells made according to the present invention can be administered to a patient undergoing a heart attack thereby increasing the oxygen delivery to the ischemic heart tissue and, at the same time, reducing the cardiac output. The IHP-loaded red blood cells made according to the present invention also can be used to treat any ischemic condition including, but not limited to, "bleeding" anemia, surgical complications, stroke, diabetes, sickle cell disease, burns, intermittent claudication, emphysema, hypothermia, peripheral vascular disease, congestive heart failure, angina, transient ischemic disease, disseminated intravascular coagulation, adult respiratory distress syndrome (ARDS) and cystic fibrosis. A detailed description of the medical applications of compositions prepared in accordance with the method of the present invention is also provided below.

In one embodiment of the present invention, substances or drugs can be introduced into cells or fragments of cells such as platelets. For example, thrombus dissolving substances such as tissue plasminogen activator, urokinase or streptokinase and the like can be introduced into a population of platelets. Tissue plasminogen activator is sold under the trademark ACTIVASE® by Genentech Corporation, South San Francisco, Calif. These platelets loaded with the thrombus dissolving substances can be then introduced into a patient who is suffering from a thrombus blocking a blood vessel. The platelet containing the thrombus dissolving substance will then migrate to the site of the thrombus and attach itself to the thrombus. Because the treated platelets contain active thrombus dissolving enzymes, the thrombus is then dissolved. It is to be understood that other drugs can be introduced into the platelets or other cells for delivery to damaged tissue. These drugs include, but are not limited to, antibiotics, smooth muscle inhibitors, antifungal agents, antiviral agents, chemotherapeutic agents and the like. Antiangiogenic drugs can be incorporated into the platelets. Antiangiogenic drugs include, but are not limited to, AGM-1470 (TNP-470) or antagonists to one of its receptors MetAP-2; growth factor antagonists or antibodies to growth factors (including VEGF or bFGF); growth factor receptor antagonists or antibodies to growth factor receptors; inhibitors of metalloproteinases including TIMP, batimastat (BB-94), and marimastat; tyrosine kinase inhibitors including genistein and SU5416; integrin antagonists including antagonists alphaVbeta3/5 or antibodies to integrins; retinoids including retinoic acid or the synthetic retinoid fenretinide; steroids 11α-epihydrocortisol, corteloxone, tetrahydrocortisone and 17α-hydoxyprogesterone; protein kinase inhibitors including staurosporine and MDL 27032; vitamin D derivatives including 22-oxa-1 alpha, and 25-dihydroxyvitamin D3; arachidonic acid inhibitors including indomethacin and sulindac; tetracycline derivatives including minocycline; thalidomide derivatives; 2-methoxyestradiol; tumor necrosis factor-alpha; interferon-gamma-inducible protein 10 (IP-10); interleukin 1 and interleukin 12; interferon alpha, beta or gamma; ANGIOSTATIN® protein or plasminogen fragments; ENDOSTATIN™ protein or collagen 18 fragments; proliferin-related protein; group B streptococcus toxin; CM101; CAI; troponin I; squalamine; nitric oxide synthase inhibitors including L-NAME; thrombospondin; wortmannin; amiloride; spironolactone; ursodeoxycholic acid; bufalin; suramin; tecogalan sodium; linoleic acid; captopril; irsogladine; FR-118487; triterpene acids; castanospermine; leukemia inhibitory factor; lavendustin A; platelet factor-4; herbimycin A; diaminoantraquinone; taxol; aurintricarboxylic acid; DS-4152; pentosan polysulphite; radicicol; fragments of human prolactin; erbstatin; eponemycin; shark cartilage; protamine; Louisianin A, C and D; PAF antagonist WEB 2086; auranofin; ascorbic ethers; and sulfated polysaccharide D 4152. The agents, including thrombus dissolving substances, can be introduced into the platelets by a variety of methods with the most preferable method being according to the apparatus of the present invention as described herein.

Patients that can be treated with the modified platelets include, but are not limited to, heart attack patients, patients suffering a stroke, and any patient that is suffering from an embolism. The amount of thrombus dissolving substance that is introduced into a platelet is between 0.01 $\mu$g to 1 mg per platelet. Generally speaking, one loads as much thrombus dissolving substance as possible into a population of platelets. The method of introducing the thrombus dissolving substance into the platelets is similar to the method of introducing IHP into red blood cells as described herein.

The present invention also includes methods and compositions for delivering bioactive compounds to the body by loading red cells, white cells and/or platelets with agents including, but not limited to, cytokines, such as inteferon, colony stimulating factors, and interleukins; hormones, such as growth hormone, insulin, and prolactin; antibodies, including monoclonal antibodies and polyclonal antibodies as well as antibodies conjugated to toxins radioactive agents; chemotherapeutic agents, such as doxirubicin, amphotericin, and taxol, bioactive peptides, and antiviral agents.

Another embodiment of the present invention is the targeting of therapeutic agents to certain locations in the body by loading a particular cell with a therapeutic agent or agents. Examples of this embodiment include, but are not limited to, loading of platelets with an antiangiogenic agent that will be targeted to a site that has been treated mechanically to remove an atherosclerotic plaque (as in angioplasty) and loading of leukocytes with antibiotics which that migrate to a site of an infection.

Another embodiment of the present invention is a preparation of red blood cells that has a stable $P_{50}$ or maintains a higher $P_{50}$ value than untreated red blood cells stored under similar conditions. Untreated freshly drawn red blood cells will have a $P_{50}$ of approximately 27 mm Hg. This value decreases over time as it is stored in the blood bank at 2–8° C. due to the loss of the allosteric effector 2,3, diphosphoglycerate. After several days in storage the $P_{50}$ drops to around 22–25 mm Hg. After 1 to 2 weeks the value can drop to around 18–20 mm Hg. It is contemplated as part of the present invention a preparation of isolated red blood cells that have a $P_{50}$ greater than approximately 30 mm Hg. These red blood cells have a stable $P_{50}$ that remains substantially the same over the storage life of the red blood cell. Thus, one embodiment of the present invention is an isolated preparation of red blood cells that can be stored under normal blood bank conditions, e.g., 2–8° C., and has a substantially stable $P_{50}$ of greater than approximately 30 mm Hg, more desirably greater than approximately 35 mm Hg, even more desirably greater than approximately 40 mm Hg and most desirably greater than approximately 45 mm Hg.

It is further contemplated as part of the present invention that the red blood cells that have a substantially stable elevated $P_{50}$ have been treated with IHP so that the IHP passes through the red blood cell membrane so that it can bind to the DPG binding site of hemoglobin. The method of introducing the IHP into the interior of the red blood cell membrane can be by any method that will produce a substantially stable preparation of red blood cells with an elevated $P_{50}$. For example, the red blood cells can be treated as described herein by flow electroporation in the presence of IHP, or the red blood cells can be exposed to hypo or hyper osmotic agents to allow a chemical such as IHP to pass through the red cell membrane so that the IHP molecule can bind to the DPG binding site.

In addition, the red blood cell preparation can be a population of normal, untreated red blood cells that naturally have an elevated $P_{50}$ level. A population of normal, untreated red blood cells that has an elevated $P_{50}$ level can be isolated by density gradient fractionation methods as well as by other methods. Thus, one embodiment of the present invention includes a volume of red blood cells, such as a unit (1 unit=453 ml±50 ml), that has an overall right shift of greater than preferable 30 mm Hg, more desirably greater than 35 mm Hg, even more desirably greater than 40 mm Hg and most preferably greater than 45 mm Hg to 50 mm Hg and the right shift is substantially stable over a period of at least 4 days, desirably 7 days, preferably 14 days and most desirably 21 days. The term "substantially stable" as used herein means a decrease in the $P_{50}$ of the red blood cell population of less than 10% per day, desirably less than 5% per day and more desirably less than 3% per day. It is contemplated as part of the present invention that the volume of blood can be any volume that would be used in storing the blood and includes, but is not limited to, 100 ml, 250 ml, 500 ml and 900 ml.

The present invention includes a method of gene therapy including, but not limited to the introduction of deoxyribonucleic acid and ribonucleic acid preparations into live cells. The DNA and/or RNA preparations preferably code for a desired protein or fragment of a protein and the DNA can optionally contain vectors that will facilitate the introduction of the DNA into the genetic mechanisms of the cell and thereby increase the expression of the desired protein. These methods of adding vectors to naked DNA preparations are well known to those of ordinary skill in the art. The DNA that is introduced using the flow electroporation apparatus of the present invention can be naked DNA or can contain other agents to facilitate entry of the DNA into the cell.

Continuous Flow Encapsulation Apparatus

The method of operation of the apparatus of the present invention is described below with reference to the preferred use of the apparatus, i.e., the encapsulation of allosteric effectors of hemoglobin in red blood cells by electroporation. It is to be understood that the apparatus may be adapted to accommodate other cell populations or vesicles, and other biologically active substances. Additionally, the apparatus maybe adapted to utilize methods of encapsulation other than electroporation.

Briefly, in accordance with the present invention, a sample of blood is introduced into the continuous flow encapsulation apparatus. If red blood cells are being collected, the blood can either be drawn directly from a patient or can be previously drawn blood. The blood is initially separated into red blood cells, plasma and white blood cells, and waste products. The waste products include the diluent and various blood solutes remaining in the supernatant after centrifugation. They are stored in a waste reservoir within the apparatus. The blood plasma and white blood cells are also retained in a reservoir within the system while the red blood cells are admixed with the substance to be encapsulated. The suspension of red blood cells is then subjected to electroporation. Following electroporation, the red blood cells are incubated under conditions which allow the cells to reseal. They are then processed and washed to eliminate exogenous, non-encapsulated biologically-active substances. When the cells have been processed, the red blood cells containing the encapsulated substances can be optionally reconstituted with the blood plasma and white blood cells. The reconstituted blood may then be returned directly to the patient or can be stored for later use. Although described as discrete steps, the process is essentially continuous.

A first embodiment of the present invention is described with reference to FIG. 1, which schematically illustrates the structure of the continuous flow encapsulation apparatus of the present invention.

In accordance with the present invention, a volume of whole blood is admitted into the electroporation system 5 at input 11. The blood sample may optionally be drawn directly from a patient into the electroporation system 5, or die blood may be drawn at an earlier time and stored prior to introduction into the system 5. Valve 12 is opened to admit the sample into the system 5. Simultaneously, valve 25 is opened and pump 22 is engaged to admit an anti-coagulant from the anti-coagulant reservoir 27. A suitable anticoagulant is heparin, although other anticoagulants can be used. The preferred anticoagulant is ACD. Valves 15 and 36 are also opened and pump 40 is engaged. The admixture of anticoagulant and whole blood passes through a filter 18 and a pressure evaluation system 19 that monitors the flow through the apparatus, and is collected in a blood separation and wash bowl 44 which is activated when pump 40 is engaged. A sensor indicates when the blood separation and wash bowl 44 has been filled with red blood cells. When it has been filled, the blood supply is stopped. The steps involving separation of the blood components can be accomplished by a plasmaphoresis apparatus, such as the plasmaphoresis apparatus manufactured by Haemonetics Corporation (Haemonetics Corporation, Braintree, Mass.).

As explained above, when pump 40 is engaged in a clockwise direction, the blood separation and wash bowl 44 is engaged and the anti-coagulant and whole blood suspension is centrifuged to separate the plasma, white blood cells, red blood cells, and waste. Valve 87 is opened to admit the plasma and white blood cells into the plasma reservoir 89.

Optionally, and dependent on the cell population being processed by the apparatus, the cells retained in the blood separation and wash bowl 44 are then washed. Valves 33, 15, and 36 are opened to admit saline buffer from the diluent reservoir 30 into the blood separation and wash bowl 44 which contains the red blood cells. Pump 40 is still engaged. The red blood cells are then washed and centrifuged. The preferred saline buffer is a 0.9% sodium chloride solution, although other physiologically isotonic buffers can be used to dilute and wash the red blood cells. Valve 54 is opened to admit the waste into the waste reservoir 57 during the washing process. Again, the waste is stored in the waste reservoir 57 and the red blood cells are retained in the blood separation and wash bowl 44. The wash process is repeated if necessary.

It has been found through experiments conducted with a variety of changes in pulse lengths and field strengths that square pulses result in less-efficient encapsulation of IHP into human erythrocytes. The creation of large pores in the cell membrane appears to be insufficient for the entry of extracellular IHP into red blood cells. This suggests a more complex process than the diffusion of IHP into the cells after the creation of the pores. It is proposed that the electrical pulse has to accomplish two tasks. The first is the generation of pores in the cell membrane and the second is the active electrophoretic movement of the IHP through those pores into the red blood cell. This can be accomplished through the use of high voltage square pulses (2.0 to 5.0 kV/cm, 2 ms) immediately followed by a lower voltage exponential pulse (0.5 to 1.95 kV/cm, 5 ms), which leads to an increased encapsulation of IHP into red blood cells of up to 50% of the usual expontential pulse protocol encapsulation. The exponential pulse itself is well below the electroporation threshold. Both tasks, namely pore formation and electrophoretic movement, can be most effectively accomplished with use of exponential pulses. Another embodiment is to first expose the cells to a high voltage square pulse and then a series of lower voltage pulses which tend to drive the IHP into the red blood cells resulting in a more efficient loading of the IHP into the cells. In use, the cells traveling through the electroporation chamber of the present invention are exposed to a series of pulse trains. The pulse train is between 30 and 600 pulses with the preferable number of 100, and a more preferable number 64 pulses. After each pulse in a pulse train, the polarity is changed. For any given cell as it travels the length of the electroporation chamber, preferably 2–12, or more preferably 3–8 and most preferably 8 pulse trains are applied reversing the polarity between each pulse.

Following separation of the red blood cells, pump 40 is reversed, pump 22 is turned off, valves 12, 15, 33, 36, 25, 87, and 54 are closed, and valves 97 and 64 are opened. The IHP solution is pumped out of the IHP reservoir 50 while, simultaneously, red blood cells are pumped out of the blood separation and wash bowl 44 towards the cooling coil 68. The red blood cells and IHP solution are admixed in the tubing of the apparatus at junction 67 and then pumped through the cooling coil 68. In a preferred embodiment of the present invention, and as explained in detail below, the IHP solution and red blood cells may be admixed in the separation and wash bowl 44 before being admitted into the cooling coil 68.

The preferred concentration of IHP in the solution is between approximately 10 mMol and 100 mMol with a more preferred concentration of approximately 22.5 to 50 mMol, and a most preferred concentration of 35 mMol. The preferred concentration of KCl in the IHP solution is between approximately 10 mM and 5 mM. The preferred concentration of $MgCl_2$ is between approximately 2 mM and 0.5 mM. The preferred concentration of sucrose in the IHP solution is between approximately 67.5 mM and 270 mM. It is to be understood that other sugars or polymers can be used as a substitute for sucrose. It is to be understood that the blood preparation can optionally be subjected to an oxygenation step by introducing the blood to a solution that is saturated or partially saturated with oxygen.

The solutions that are used in the present invention are resistance enhancing fluids. It is important to note that the IHP solution should have a high resistivity and should have a minimum of electrolytes. The IHP from Aldrich Chemical Company or from Matrea Chemical Company does not contain any sodium chloride and a minimum of other electrolytes and therefore does not significantly decrease the resistivity of the solution. The milliosmolarity of the solution should be between approximately 270 and 500. The resistivity should be between approximately 87 mΩ·cm and 185 Ω·cm. The conductivity should be between approximately 4 to 9 mS/cm. The practical salinity should be between approximately 4 and 9 ppt and the NaCl equivalent should be between approximately 4.5 and 9.0 ppt.

The hematocrit of the suspension is preferably between approximately 30 and 80 with the most preferred hematocrit of approximately 40. It has been determined from red cell responses that the high voltage should not exceed 800 volts in the static cell (whose gap is 0.4 cm), which corresponds to 2 kv/cm. For the flow cell, which has a 0.3 cm gap, the voltage across the cell will be limited to 740 volts, (+/− 370v). A number of different electroporation fluid compositions have been tested. Table A lists six samples and their characteristics. The solution under E is the preferred electroporation solution. Pump 40 is designed to pump both red blood cells and IHP solution and can be adjusted so that the final hematocrit entering the cooling coil 68 can be predetermined.

TABLE A

|  | A[a] | B[b] | C[c] | D[d] | E[e] | CBR[f] |
|---|---|---|---|---|---|---|
| Conductivity (mS/cm) | 2.78 | 8.92 | 11.2 | 8.67 | 7.07 | 16.8 |
| Resistivity (ohm-cm) | 361 | 112 | 89.1 | 115 | 134 | 59.3 |
| mOsm | 379 | 472 | 408 | 397 | 314 | 452 |
| Practical Salinity (ppt) | 1.54 | 5.43 | 6.91 | 5.24 | 4.45 | 11 |
| NaCl Equivalent (ppt) | 1.71 | 5.43 | 6.76 | 5.25 | 4.59 | 10.2 |
| pH | 7.39 | 7.346 | 7.185 | 7.316 | 7.4 | 7.42 |
| Phytic Acid (IHP) | Aldrich IHP | Sigma IHP | Aldrich IHP | Aldrich IHP | Matreya IHP | Sigma IHP |

[a] 10 mmol KCl, 2 mm $MgCl_2$ 270 mmol Sucrose, 35 mmol IHP
[b] Same as A except with potassium salt of IHP
[c] Iscove's Mod. Dulbecco's 125 mmol Su
[d] Dulbecco's phosphate buffered saline, 125 mmol Sucrose
[e] 5 mmol KCl, 1 mmol $MgCl_2$, 135 mmol sucrose
[f] 33 mmol $K_2HPO_4$, 7.0 mmol $NaH_2PO_4$, 30.6 mmol KCl, 6.4 mmol NaCl, 7.3 mmol sucrose, 5.0 mmol ATP
[g] 35 mm IHP, 5 mm KCl, 0.5 mM $MgCl_2$, 100 mM sucrose After mixing, the red blood cell-IHP suspension is then pumped through a cooling coil 68. Cooling can be achieved with a water bath or with a thermo-electric based cooling system. For example, cooling coil 68 is immersed in a cooling bath in the cooling reservoir 69. When the red blood cell-IHP suspension passes through the cooling coil 68, the suspension is cooled to a temperature of between approximately 1° C. and 12° C., preferably approximately 4° C. Cooling the red blood cells ensures the survival of the pore created in the cell membrane during the electroporation process. The use of a cooling coil aids in the speed of cooling by increasing the surface area of the sample in contact with the cooling element. Optionally, the cooling coil can be surrounded by a thermo-electric heat pump.

Certain applications may require heating of the cell suspension prior to electroporation. In such a case, a heating coil may replace the cooling coil 68. The maximum temperature tolerated by red blood cells is approximately 42° C.

A thermoelectric heat pump works by extracting thermal energy from a particular region, thereby reducing its temperature, and then rejecting the thermal energy into a "heat sink" region of higher temperature. At the cold junction, energy is absorbed by electrons as they pass from a low energy level in the p-type semiconductor element, to a higher energy level in the n-type semiconductor element. The power supply provides the energy to move the electrons through the system. At the hot junction, energy is expelled into a heat sink as electrons move from a high energy level element (n-type) to a lower energy level element (p-type).

Thermoelectric elements are totally solid state and do not have moving mechanical parts or require a working fluid, as do vapor-cycle devices. However, thermoelectric heat pumps perform the same cooling functions as freon-based vapor compression or absorption refrigerators. Thermoelectric heat pumps are highly reliable, small in size and capacity, low cost, low weight, intrinsically safer than many other cooling devices, and are capable of precise temperature control.

The preferred thermoelectric heat pumps for use in the present invention are manufactured by MELCOR Materials Electronic Products Corp. of Trenton, N.J. The thermocouples are made of high performance crystalline semiconductor material. The semiconductor material is bismuth telluride, a quaternary alloy of bismuth, tellurium, selenium, and antimony, doped and processed to yield oriented polycrystalline semiconductors with properties. The couples, connected in series electrically and in parallel thermally, are integrated into modules. The modules are packaged between metallized ceramic plates to afford optimum electrical insulation and thermal conduction with high mechanical strength in compression. Modules can be mounted in parallel to increase the heat transfer effect or can be stacked in multiple-stage cascades to achieve high differential temperatures. Passing a current through the heat pump generates a temperature differential across the thermocouples, with maximum ratings of 70° C. and higher.

After cooling, the red blood cell-IHP suspension enters the electroporation chamber 72 where an electric pulse is administered from a pulse generator 75 to the red blood cell-IHP suspension, causing openings to form within the cell membranes of the red blood cells. Optionally, an automatic detection system will turn the pulse generator 75 on when the chamber 72 is filled with red blood cell-IHP suspension. An electrical pulse is applied to the suspension every time the chamber 72 is filled with unencapsulated cells. A conventional electroporation chamber may be used when the operation of the apparatus is static, namely, when single discrete batches of cells are processed. In a preferred embodiment of the present invention a flow electroporation chamber is used. In one embodiment, a flow electroporation chamber 72 is constructed of clear polyvinyl chloride, and contains two opposing electrodes spaced a distance of 7 mm apart. The distance between the electrodes will vary depending on the flow volume and field strength. Preferably, the flow electroporation chamber 72 is disposable. The electroporation chamber may also be constructed of polysolfone, which is preferably for use with certain sterilization procedures, such as autoclaving. A detailed description of the structure and construction of the flow electroporation chamber is provided below.

The red blood cell-IHP suspension passes between the two electrodes of the electroporation chamber 72. When a suspension of non-treated cells enter the chamber 72, an electrical field of approximately 1 to 4 KV/cm is created for a period of approximately 0–60 milliseconds, preferably for a period of 40 milliseconds in a 1.2 ml flow chamber. Preferably, the IHP-red blood cell suspension is subjected to 8 high voltage pulse trains at a field strength of approximately 2.0 to 5.0 kV/cm high voltage pulses followed by lower voltage pulses of approximately 0.5 to 1.95 kV/cm per pulse. Each of the pulse trains is composed of 64 pulses with each pulse having an on time of 150 $\mu$sec and an off time of 475 $\mu$sec. Preferably, the power system is set to "energy savings mode" to prevent unnecessary heating and thus destruction of blood cells. The preferred representation of this mode is a 4×4×64 pulse train. This indicates that 4 alternating polarity DC pulses are applied to the suspension after which another 4 pulses are applied at a reduced-time constant tau$^2$ after which the remaining 56 pulses are applied at the original time constant tau. The pulse of current across the cell membranes causes an electrical breakdown of the cell membranes, which creates pores in the membranes. IHP then diffuses into the cell through these pores.

Following electroporation, the red blood cell-IHP suspension enters an incubation chamber 78 where the suspension is incubated at room temperature for an incubation time of between approximately 15 minutes and 120 minutes with the preferred incubation time of 30 to 60 minutes. Optionally, the red blood cell-IHP suspension is incubated for approximately 5 minutes at a temperature of approximately 37° C., and at least 15 minutes at room temperature. The incubation chamber 78 may optionally be surrounded by a heating means 80. For example, the heating means 80 can be a water bath or can be a thermoelectric heat pump.

Optionally, the incubator 78 contains a resealing buffer which aids in resealing and reconstitution of the red blood cells. The preferred composition of the resealing buffer is provided below in Table B:

TABLE B

RESEALING BUFFER

| I. Combine | |
| --- | --- |
| Sodium chloride | 150 mMol |
| Potassium chloride | 5 mMol |
| Sodium phosphate | 6 mMol |
| Magnesium sulfate | 2 mMol |
| Glucose | 10 mMol |
| Adenine | 1 mMol |
| Inosine | 1 mMol |
| Penicillin G | 500 units/ml |
| Chloramphenicol | 0.2 mg/ml |
| II. Add | |
| BSA | 3.5% |
| Calcium chloride | 2 mMol |

In the preferred embodiment of the present invention, no resealing buffer is used.

Following incubation, valve 51 is opened and pump 40 is engaged and the red blood cell-IHP suspension is returned to the blood separation and wash bowl 44 from the incubation chamber 78. The excess IHP solution is removed from the red blood cell suspension by centrifugation. The waste IHP solution is directed to waste reservoir 57. Valves 33, 15 and 36 are then opened to admit a volume of diluent into the blood separation and wash bowl 44. A diluent that can be used in the present invention is shown in Table C.

TABLE C

DILUENT BUFFER

| I. Combine | |
| --- | --- |
| Sodium chloride | 0.9% |
| Magnesium chloride | 2 mM |
| Calcium chloride | 2 mM |
| Magnesium sulfate | 2 mMol |
| Glucose | 10 mMol |
| 0.1% Penicillin (Optional) | 0.1% |
| 0.1% Streptomycin (Optional) | 0.1% |

The red blood cell-IRP suspension is then centrifuged and the supernatant is discarded in the waste reservoir 57 through valve 54 leaving the red blood cells in the blood separation and wash bowl 44. A saline buffer is added to the modified red blood cells from the diluent reservoir 30. The cells are washed and the supernatant is discarded following centrifugation. The wash process is repeated if needed.

Optionally, as the waste is removed from the separation and wash bowl 44 it passes through a contamination detector 46 to detect any free IHP in the waste solution thereby confirming that exogenous non-encapsulated IHP has been removed from the modified red blood cells. The contamination detection system relies on optical changes in the washing buffer. After the modified red blood cells have been washed and centrifuged, the supernatant passes through the contamination detector 64 before it is deposited in the waste reservoir 57. If exogenous, non-encapsulated IHP remains in the washing buffer, The discarded solution will be turbid. The turbidity is due to the reaction of IHP with calcium, which is a component of the wash buffer. The contamination detector 46 uses an optical detection system. Preferably, the light source is an LED and the detector is a photodiode. The voltage difference of the photodiode will indicate the amount of IHP in the wash solution. The contamination detector 46 is optional.

Following washing, the IHP-red blood cell product is optionally reconstituted with the plasma and white blood cells which had been retained in reservoir 89. The treated red blood cells may be collected in a reinjection bag, either in a preservation media or in the autologous plasma of the patient.

The IHP-loaded red blood cells obtained can be administered directly back into the patient or the cells can be stored for later use. The IHP in the red blood cells is not released during the normal storage time.

Figure 2:
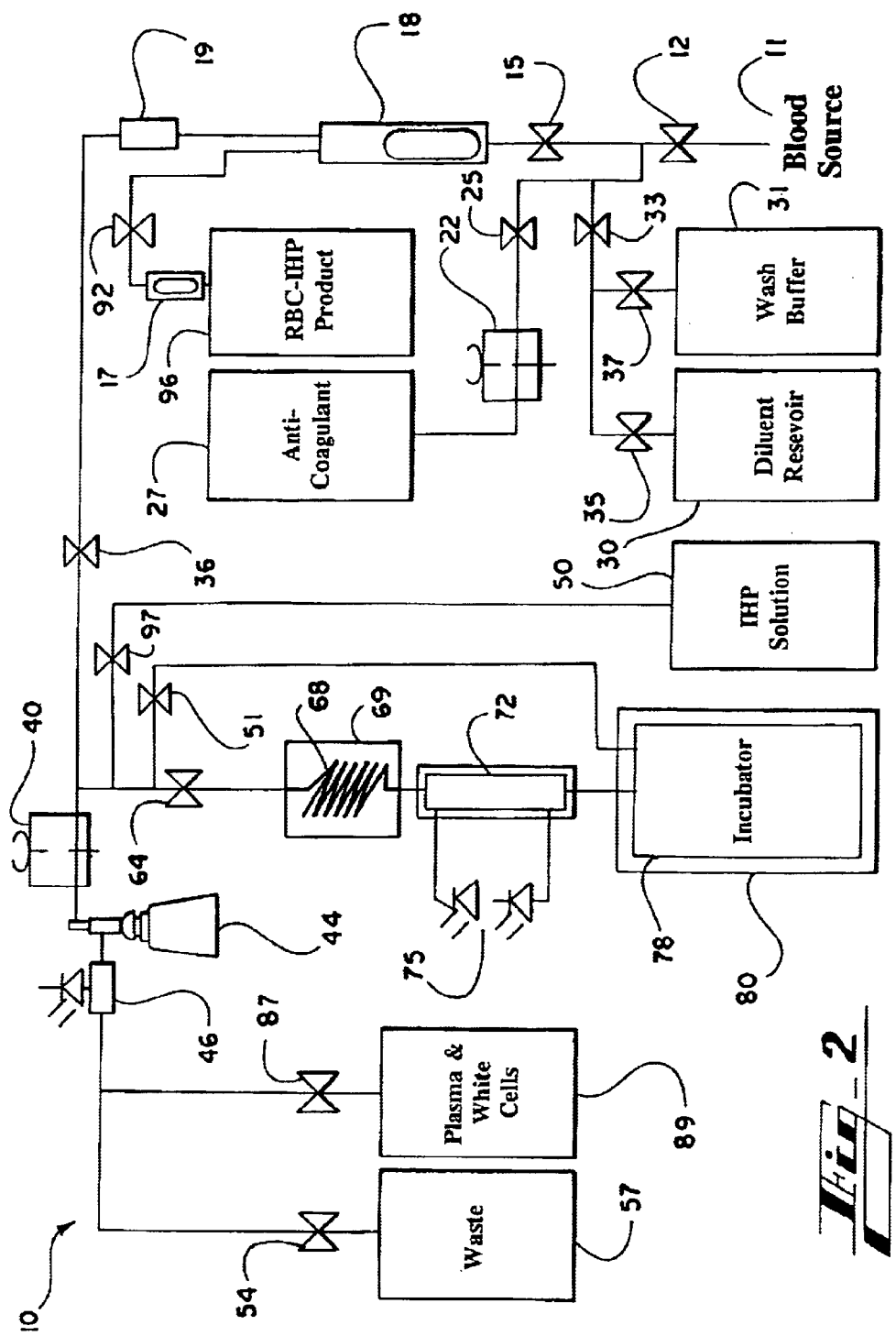
FIG. 2 is a schematic diagram of a second embodiment of a continuous flow encapsulation apparatus.

A preferred embodiment of the present invention is described with reference to FIG. 2, which schematically illustrates the structure of the continuous flow encapsulation apparatus of the present invention. Again, the method of operation of the apparatus is described with reference to the preferred use of the apparatus, i.e., the encapsulation of allosteric effectors of hemoglobin in red blood cells by electroporation. It is to be understood that the apparatus may be adapted to accommodate other cell populations or vesicles, and other biologically active substances. Additionally, the apparatus maybe adapted to include other methods of encapsulation.

In accordance with the present invention, a sample of whole blood is admitted into the electroporation system 10 at input 11. Valve 12 is opened to admit the sample into the system 10. Simultaneously, valve 25 is opened and pump 22 is engaged to admit an anti-coagulant from the anti-coagulant reservoir 27. Valves 15 and 36 are also opened and pump 40 is engaged.

The admixture of anticoagulant and whole blood passes through a filter 18 and a pressure evaluation system 19, and is collected in a blood separation and wash bowl 44 which is activated when pump 40 is engaged. A sensor indicates when the blood separation and wash bowl 44 has been filled with red blood cells.

When pump 40 is engaged in a clockwise direction, the blood separation and wash bowl 44 is engaged and the anti-coagulant and whole blood suspension is centrifuged to separate the plasma, white blood cells, red blood cells, and waste. Valve 87 is opened to admit the plasma and white blood cells into the plasma reservoir 89.

Optionally, the cells retained in the separation and wash bowl 44 are then washed and centrifuged. Valves 33, 35, 15, and 36 are opened to admit saline buffer from the diluent reservoir 30 into the blood separation and wash bowl 44 which contains the red blood cells. Valve 12 is closed and pump 40 remains engaged.

During washing, valve 54 is opened to admit the waste into the waste reservoir 57 during the washing process. Again, the waste is stored in the waste reservoir 57 and the red blood cells are retained in the blood separation and wash bowl 44. The wash process is repeated if necessary. A contamination detection system may optionally be installed between the separation and wash bowl 44 and the waste reservoir 57 to control the wash process.

Following separation of the red blood cells, pump 40 is reversed, pump 22 is turned off, valves 12, 15, 33, 35, 36, 25, 87, and 54 are closed, and valve 97 is opened. If the cells were washed, pump 22 was previously turned off and valves 12 and 25 had been closed. The IHP solution is pumped out of the IHP reservoir 50 and into the separation and wash bowl 44 containing the red blood cells. There, the red blood cells and IHP are admixed to form a suspension.

The preferred concentration of IHP in the solution is between approximately 10 mMol and 100 mMol with a more preferred concentration of approximately 23 to 35 mMol, and with a most preferred concentration of 35 mMol. The preferred IHP solution comprises the following compounds, in the following concentrations:

35 mM IHP (Hexasodium salt) neutralized (Norquay Technology Inc.

5 mM KCl 0.5 mM $MgCl_2$ 135 mM sucrose

Figure 22:
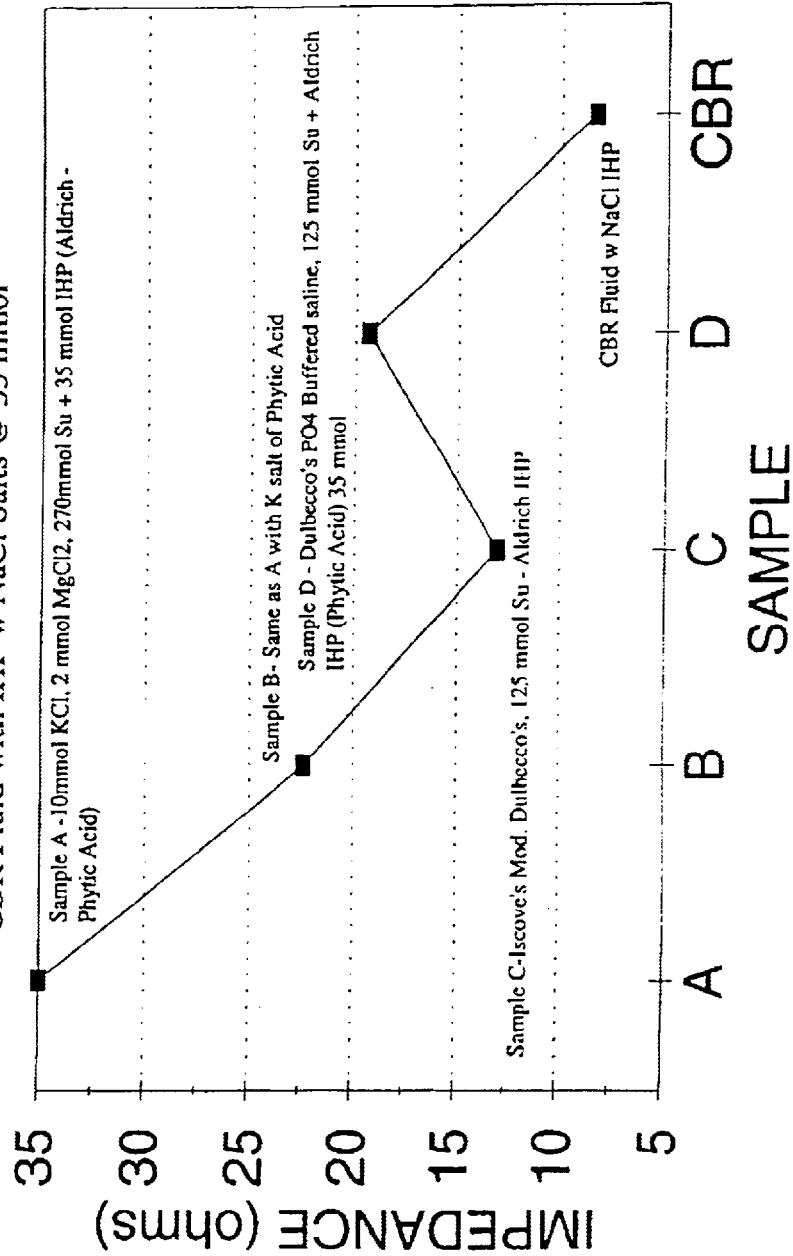
FIG. 22 is a graph showing the resistance of several IHP solutions.

The IHP from Aldrich Chemical Company does not contain any sodium chloride and a minimum of other electrolytes and therefore does not significantly decrease the resistivity of the solution. It is to be understood that other solutions with high impedance can be used in the present invention and that the components of the solution are not critical. As long as the osmotic properties of the solution are such that the cells, such as red blood cells are not damaged, and the resistivity of the solution is high, it is suitable for use in the present invention. Several compostions were tested for resistivity and are shown in FIG. 22. The "CBR Fluid" is shown in Table A.

The hematocrit of the suspension is preferably between approximately 30 and 60 with the most preferred hematocrit of approximately 40. Pump 40 is designed to pump both red blood cells and IHP solution and can be adjusted so that the final hematocrit entering the cooling coil 68 can be predetermined.

After combining the red blood cells with the IHP solution, pump 40 is again reversed, valve 97 is closed and valve 64 is opened. The red blood cell-IHP suspension is then pumped through a thermoelectric cooling coil 68. A blood bag from a blood warming set, such as the blood bag provided in the Fenwal® Blood Warming Set manufactured by Baxter Healthcare Corporation can be used as the cooling coil 68. When the red blood cell-IHP suspension passes through the cooling coil 68 in the cooling reservoir 69, the suspension is cooled to a temperature of between approximately 1° C. and 12° C., preferably approximately 4° C. Optionally, a pump may be added to the apparatus between the cooling coil 68 and cooling reservoir 69, and the electroporation chamber 72, to ensure a constant flow rate and compensate for fluctuation in volume that occurs when the cooling coil 68 is filled.

Optionally, the pre-cooling step may be eliminated and the red blood cell-IHP suspension may be directed to the electroporation chamber 72 immediately after admixing. In such an instance, the cooling coil 68 and cooling reservoir 69 would be eliminated from the continuous flow encapsulation apparatus 10. Cooling prior to electroporation may not be required if the temperature of the electroporation chamber is sufficiently cool to maintain the cells suspension at 4° C.

After cooling, the red blood cell-IHP suspension enters the electroporation chamber 72. The chamber 72 is maintained at a temperature of approximately 4° C. As the red blood cell-IHP suspension passes through the flow electroporation chamber 72, an electric pulse is administered from a pulse generator 75 to the suspension causing openings to form within the cell membranes of the red blood cells.

The red blood cell-IHP suspension passes between two electrodes of the electroporation chamber 72. FIGS. 3 to 10 describe the electroporation chamber. In a preferred embodiment of the present invention, when a suspension of non-treated cells enters the chamber 72, the IHP-red blood cell suspension is subjected to approximately three high voltage pulses per volume or pulse trains per volume at a fieldstrength of approximately 2600 to 3700 V/cm per pulse. It has been determined that for introduction of IHP into blood, instead of a single pulse, a train of short pulses is more efficient in transporting IHP into the red blood cell. The optimal number of pulses is between approximately 8 pulses with 64 pulses per train with the preferable number being approximately 64 pulses per pulse train. It is also advantageous to change the polarity of the field between pulses or pulse trains. In FIG. 28, a representative two pulse train is shown. The potential drop created across the cell membrane causes a breakdown of the membrane, which creates pores in the membrane. IHP then diffuses into the cell through these pores. In addition, although not wanting to be bound to the following hypothesis, it is believed that the IHP is actually forced into the cell in the electric field.

During electroporation, an electrical field of 1 to 3.7 KV/cm is created and maintained for a period of 1 to 4 milliseconds. The preferred pulse length is 3 to 4 milliseconds, with a most preferred pulse length of 2 milliseconds. Pulse length or pulse train length is defined as 1/e. At a flow rate of approximately 10.6 ml/minute, the preferred number of pulses is 3 to 5, at the preferred pulse rate of 0.29 Hz. The fieldstrength is defined as the voltage over the distance between the electrodes. The distance between electrodes is measured in centimeters. The preferred electrical parameters are as follows:

pulse length or pulse train length=1.5 to 2.5 ms fieldstrength=2.7 to 3.7 KV/cm pulse width=150 $\mu$sec (on) to 475 ms$^2$ (off)

pulse train length—40 ms with 64 pulses

The electroporation chamber can optionally be a sensor in the sense that the resistivity of the cell solution that is traveling through the electroporation chamber is monitored. as the resistivity of the cell solution changes, there is a feedback circuit that will adjust the pulsing of the cells to maintain optimum electroporation efficiency. For example, when electroporating blood in an IHP solution, different samples of blood may have different resistivity. By monitoring the resistivity of the blood, optimal pulse strengths and pulse timing can applied based on the resistivity measurement. In addition, if a bubble should be introduced into the electroporation chamber, the feedback circuit will sense the presence of the bubble because of the change in resistivity, and will turn off the pulsing until the bubble exits the chamber.

Following electroporation, the red blood cell-IHP suspension enters an incubation chamber 78 where the suspension is incubated at room temperature for an incubation time of between approximately 10 minutes and 120 minutes with a preferred incubation time of 30 minutes. Optionally, the red blood cell-IHP suspension is incubated for approximately 5 minutes at a temperature of approximately 37° C., and at least 15 minutes at room temperature. The incubation chamber 78 may be surrounded by a heating means 80. Any heating means 80 can be used in practicing the present invention. The preferred heating means 80 are a water bath or a thermoelectric heat pump.

Optionally, the incubator 78 contains a resealing buffer which aids in resealing and reconstitution of the red blood cells. In the preferred embodiment of the present invention, no resealing buffer is used.

Following incubation, the red blood cell-IHP suspension is returned to the blood separation and wash bowl 44 when valve 51 is opened and pump 40 is engaged. The excess IHP solution is removed from the red blood cell suspension by centrifugation. The waste IHP solution is directed to waste reservoir 57. Valves 33, 37, 15 and 36 are then opened to admit a volume of post wash solution from reservoir 31 into the blood separation and wash bowl 44. In a preferred embodiment of the present invention, the post wash solution comprises a 0.9% NaCl solution, including 2.0 mM CaCl$_2$ and 2.0 mM MgCl$_2$. Any physiological saline may be used.

After addition of the post wash solution, the red blood cell-IHP suspension is then centrifuged and the supernatant is discarded in the waste reservoir 57 through valve 54 leaving the red blood cells in the blood separation and wash bowl 44. The wash process is repeated until all unencapsulated IHP has been removed.

Optionally, as the waste is removed from the separation and wash bowl 44 it passes through a contamination detector 46 to detect any free IHP in the waste solution thereby confirming that exogenous non-encapsulated IHP has been removed from the modified red blood cells. The contamination detector 46 is optional.

Following washing, the red blood cells containing IHP may be reconstituted with the plasma and white blood cells retained in reservoir 89. Pump 40 is engaged and valves 87, 36, and 92 are opened. The modified red blood cells and plasma and white blood cells are pumped to reservoir 96. A filter may be installed between reservoir 96 and valve 92 to remove any aggregates or other impurities from the reconstituted modified blood.

The IHP-loaded red blood cells obtained in accordance with the method of the present invention can be administered directly back into the patient or the cells can be stored for later use. The IHP in the red blood cells is not released during the normal storage time.

It is contemplated that continuous flow encapsulation apparatus of the present invention may be modified to utilize other encapsulation methods.

Furthermore, it is contemplated that the continuous flow encapsulation apparatus may be adapted to process various diverse cell populations. Furthermore, the apparatus may be used to encapsulate biologically active substances in artificial vesicles.

It is also contemplated that the continuous flow encapsulation apparatus of the present invention may be used to encapsulate a broad range of biologically active substances.

Flow Electroporation Chamber

During electroporation, the insertion rate of IHP is linearly dependent on the voltage administered to the cells. Generally, the higher the voltage, the more IHP is encapsulated; however, cell lysis is also increased and cell survival is decreased. The efficiency of an electroporation system may be judged by cell survival after electroporation. Poor cell survival indicates very low efficiency. The amplitude and duration of the electrical pulse is responsible for the electric breakdown of the cell membrane and creates pores in the pole caps parallel to the electric field. Thus, the factors to be considered in designing an electroporation system include the field strength, the pulse length and the number of pulses.

A perfect electroporation target is shaped like a sphere, so its orientation does not effect the efficiency of the applied field. When the target is spherical, a single pulse with a fieldstrength above the threshold can electroplate 100% of the target. Red blood cells are disk shaped. Because of their shape and orientation in the electroporation chamber, only approximately 40% of the cells are electroplated during a single pulse. To also electroporate the other 60%, the fieldstrength can be increased. This increases the stress on the red blood cells in proper orientation to the electric field and leads to lower survival rates of the cells.

To achieve more efficient encapsulation while reducing the incidence of cell lysis and death, a flow electroporation chamber utilizing short duration multiple pulses was developed. With the flow-through rate steady and a steady field voltage, it was determined that plurality of pulses would insert maximal quantities of IHP with minimal 2 to 24 hour cell lysis. A multiple-pulse system allows an increase in the cell survival rate without increasing the field strength. When a multiple-pulse system is used, orientation of the cells is not as critical as it is when a system is a single pulse system is used. The lower fieldstrength is much more gentle to the red blood cells. It is much easier to electroporate every single cell in the multiple pulse system, because the timing between the flow rate of the red blood cells through the chamber and the electroporation pulses, and the orientation of the cells is not as crucial as in a single pulse system. The flow multiple-pulse electroporation system also increases both the short term and the long term survival of red blood cells when compared to the single pulse method.

Figure 11:
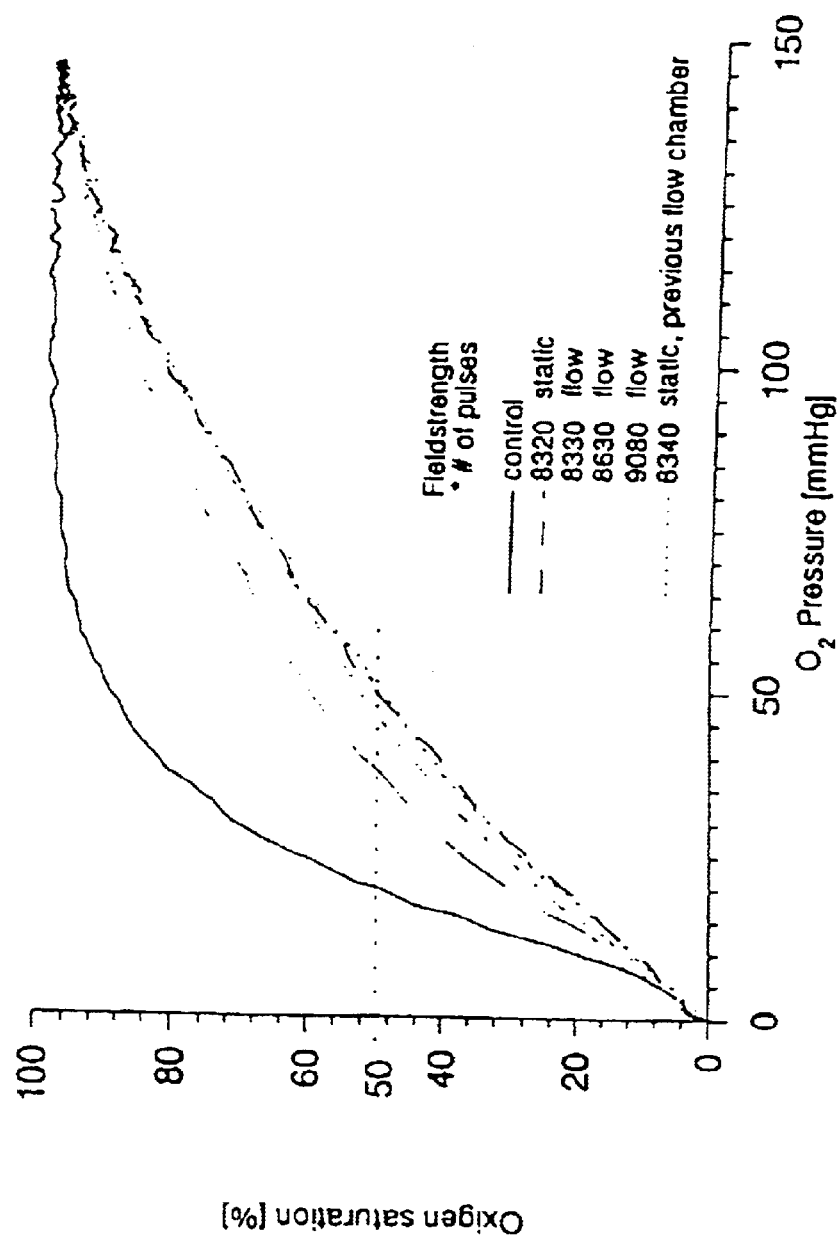
FIG. 11 is a graph comparing the effect of various field strengths, under static or flow conditions, on the % oxygenation of IHP-encapsulated red blood cells.
Figure 12:
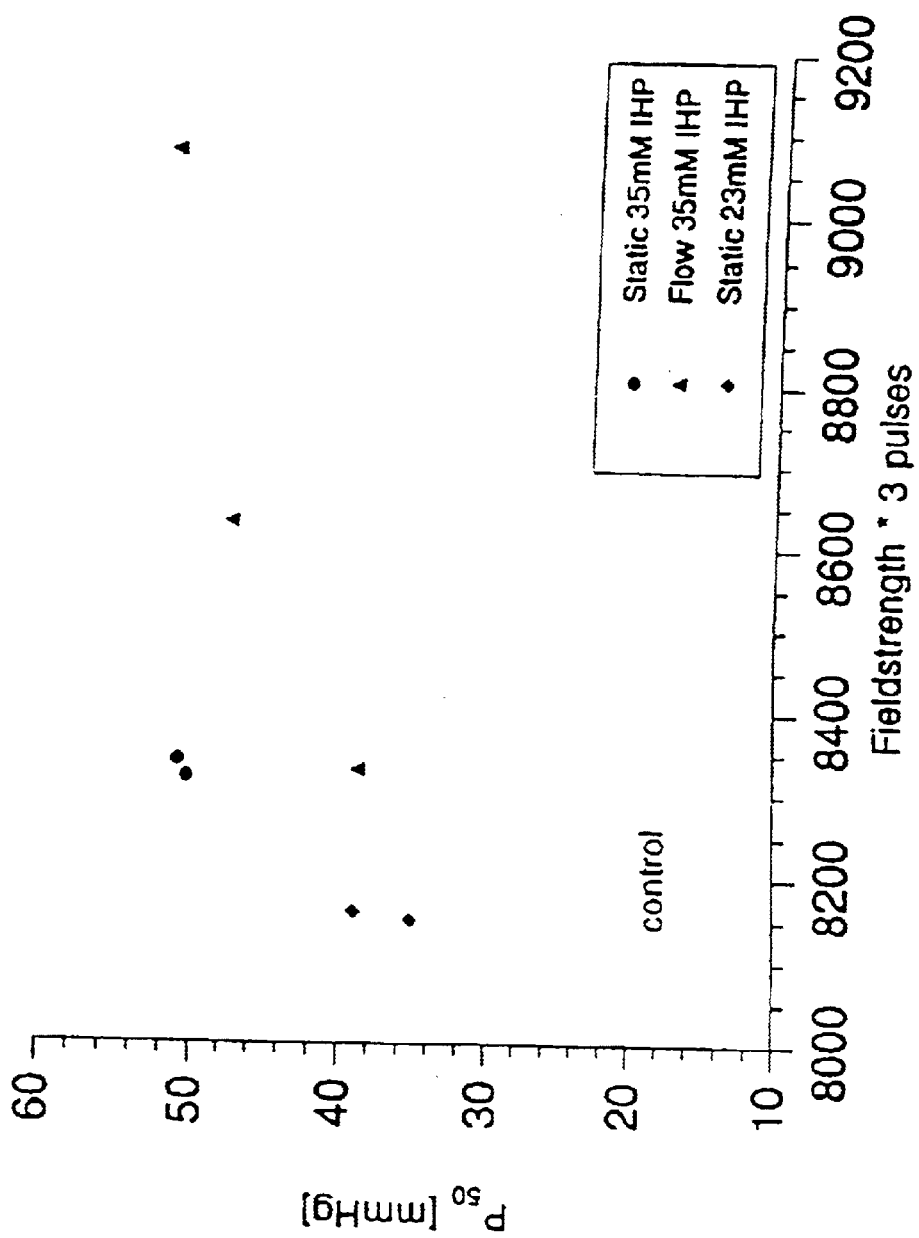
FIG. 12 is a table comparing the effects of various field strengths, under static or flow conditions, on the $P_{50}$ value of IHP-encapsulated red blood cells.
Figure 13:
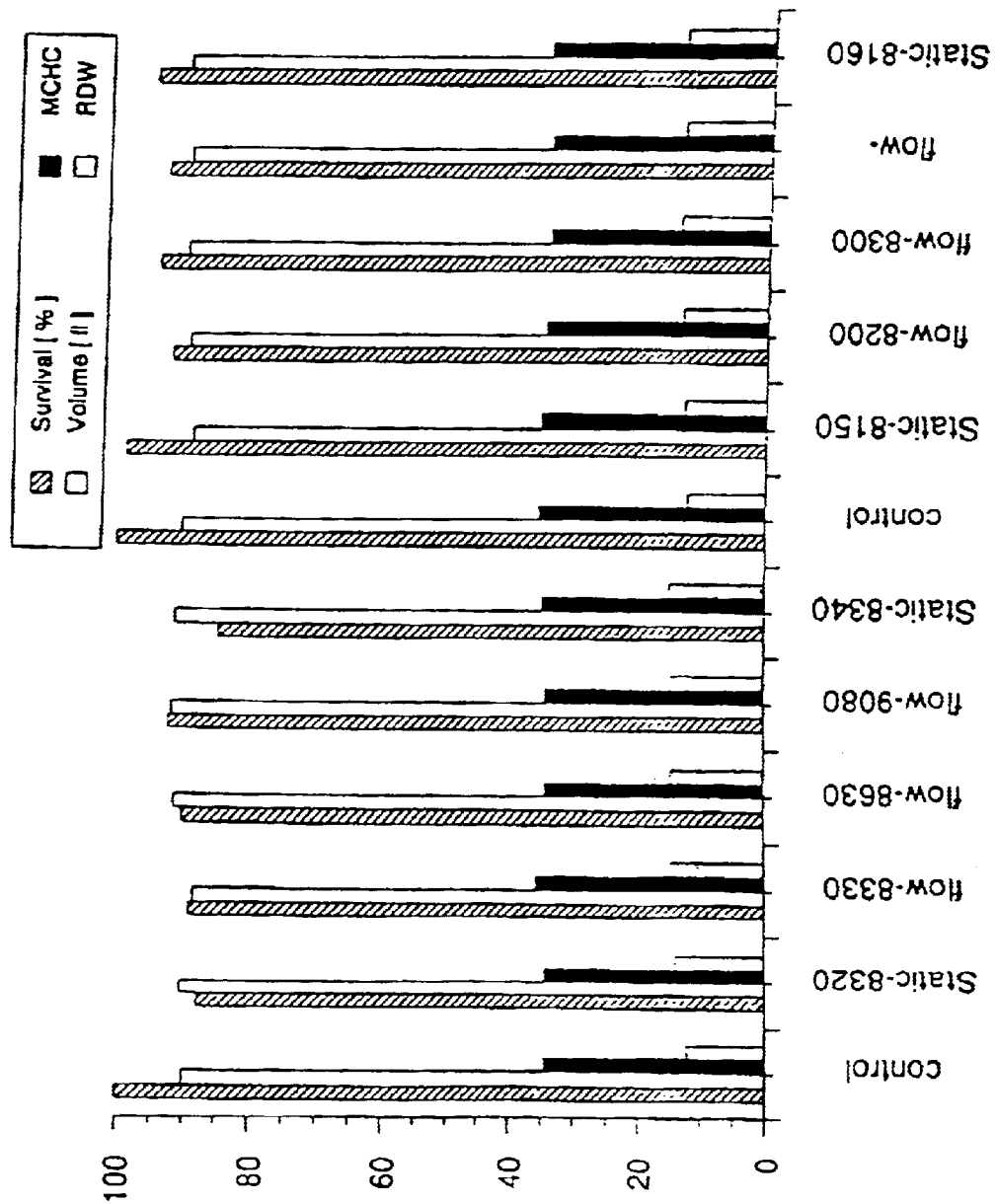
FIG. 13 is a table comparing the survival rates of red blood cells subjected to electroporation under static and flow conditions at various field strengths.

FIGS. 11 to 13 illustrate the effects of various field strengths, under static or flow conditions, on the % oxygenation of IHP-encapsulated red blood cells over a range oxygen pressures; on the $P_{50}$ value of IHP-encapsulated red blood cells (two concentrations of IHP solutions were compared); and, on the survival rates of red blood cells subjected to electroporation. All readings were taken 24 hours after electroporation. The results indicated that multiple pulses at comparatively low fieldstrengths produce optimal encapsulation results.

A cooled electroporation chamber is preferred to keep the red blood cells at a constant temperature during the electroporation process, thereby enhancing their survival rates. This is accomplished by removing the excess heat created by the electrical pulse during the electroporation process. The excess heat may be removed either by cooling the electrodes or cooling the entire flow electroporation chamber. In accordance with one embodiment of the present invention, the electrodes themselves are cooled.

During the electroporation process, blood is pumped through an inlet in the electroporation chamber and the red blood cells are subject to a series of electrical pulses as they travel through the chamber. They exit out the other end of the chamber. The chamber can be made of any type of insulating material, including, but not limited to, ceramic, Teflon, Plexiglas, glass, plastic, silicon, rubber or other synthetic materials. Preferably, the chamber is comprised of glass or polysulfone. Whatever the composition of the chamber, the internal surface of the chamber should be smooth to reduce turbulents in the fluid passing through it. The housing of the chamber should be non-conductive and biologically inert. In commercial use, it is anticipated that the chamber will be disposable.

In one preferred embodiment of the present invention, the electrodes that comprise part of the electroporation apparatus can be constructed from any type of electrically or thermally conductive hollow stock material, including, but not limited to, brass, stainless steel, gold plated stainless steel, gold plated glass, gold plated plastic, or metal containing plastic. Preferably, the surface of the electrode is gold plated. Gold plating serves to eliminate oxidation and reduces the collection of hemoglobin and other cell particles at the electrodes. The surface of the electrodes should be smooth.

The electrodes can be hollow, to allow cooling by liquid or gas, or the electrodes can be solid, to allow for thermoelectric or any other type of conductive cooling. Cooling could also be accomplished by cooling the electroporation chamber itself, apart from cooling the electrodes.

Preferably, the flow electroporation chamber is disposable. A detailed description of three embodiments of the electroporation chamber of the present invention is provided below.

In one embodiment, the flow electroporation chamber is constructed of clear polyvinyl chloride, and contains two opposing electrodes spaced a distance of approximately 7 mm apart. The electroporation chamber is a modification of a chamber obtained from BTX Electronic Company of San Diego, Calif. However, when this electroporation chamber is used continuously, it overheats and the survival rate of the cells processed by the apparatus decreases over time. To correct the overheating problem that occurred when the apparatus was used in a continuous flow manner, a continuous flow electroporation chamber was designed. A detailed description of the structure of the continuous flow electroporation chamber is provided below.

FIGS. 3 through 8 show one embodiment of the flow electroporation chamber 72 of the present invention. As can be seen in FIG. 3, the flow electroporation chamber 72 includes a housing 100 having two electrodes 102 inset on opposing sides of the housing 100 of the electroporation chamber 72. The housing 100 includes an inlet channel 104 at one end and an outlet channel 106 at the other. The inlet 104 and outlet 106 channels include connectors 108 and 109 respectively, preferably of the male Luer variety. The connectors 108 and 109 are hollow and form the inlet 104 and outlet 106 channels into the interior of the electroporation chamber 72.

As seen in FIGS. 4 and 5, an internal chamber 110 extends most of the length of the housing 100 and is sized to receive the two electrodes 102. The internal chamber 110 includes beveled surfaces 111 for receiving the internal edges of the electrodes 102. The internal chamber 110 is thus formed by the internal surfaces of the electrodes 102 and the internal surfaces of the housing 100. The internal chamber 110 is connected to the inlet 104 and outlet 106 channels.

Figures 7, 8:
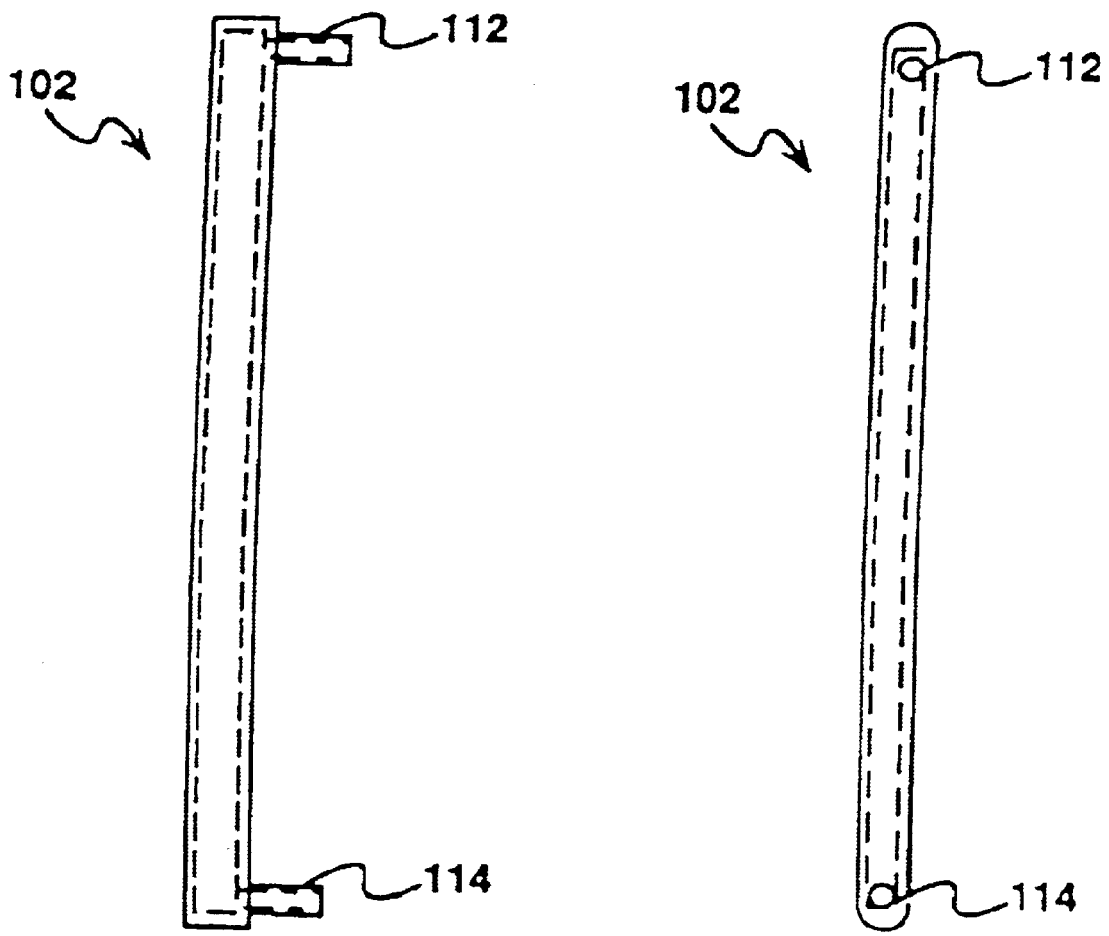
FIG. 7 is a side view of an electrode for use with the first embodiment of the flow electroporation chamber.
FIG. 8 is a front view of the electrode of FIG. 7.

As can be seen in FIGS. 7 and 8, the electrodes 102 of the electroporation chamber 72 of FIGS. 3 to 6 are comprised of flat, elongated, hollow shells. The electrodes 102 include cooling inlets 112 and cooling outlets 114 at their ends. As described above, the rear surfaces of the electrodes 102, or the surface to the left in FIG. 7, fits flush against the beveled surface 111 of the housing 100.

The electroporation chamber 72 is designed such that the cell suspension to be subjected to electroporation enters the electroporation chamber 72 through the inlet 104 and expands to fill the internal chamber 110. As the red blood cell suspension flows through the internal chamber 110 a pulse or charge is administered across the width of the internal chamber 110.

To maintain a relatively constant temperature during the electroporation process, cooling fluid or cooling gas is pumped in the cooling inlet 112 and out the cooling outlet 114 so that the electrodes 102 are maintained at approximately 4° C.

FIGS. 9 and 10 display a second embodiment of the flow electroporation chamber 172. As can be seen in FIGS. 9 and 10, the flow electroporation chamber 172 includes a hollow housing 200 substantially rectangular in shape. Two electrodes 202 are inserted into the interior of the housing 200 directly opposite one another, flush against the housing 200 walls. The flow electroporation chamber 172 further comprises an inlet channel 204 at one end and an outlet channel 206 at the other end of the housing 200. The inlet 204 and outlet 206 channels include connectors 208 and 209 which are attached by tubing 216 to a cell suspension supply that supplies the cell suspension, i.e. the IHP-red blood cell suspension, to the electroporation chamber 172. The connectors 208 and 209 and inlet 204 and outlet 206 channels serve to direct the cell suspension into and out of the housing 200.

As can be seen in FIG. 10, one end of the inlet channel 204 and one end of the outlet channel 206 extends into the interior of the housing 200 forming an internal chamber 210.

The internal chamber 210 is thus formed by the internal surfaces of the electrodes 202, the internal surfaces of the housing 200 and the internal surfaces of the of the inlet 204 and outlet 206 channels.

As can be seen in FIGS. 9 and 10, the electrodes 202 of the flow electroporation chamber 172 comprise flat, elongated, hollow shells. The electrodes 202 include cooling inlets 212 and cooling outlets 214 at their ends, through which a gas or fluid may be pumped through the electrodes 202 to maintain a constant temperature during electroporation. The electrodes 202 are connected to a pulse generator by cables 220.

As with the chamber described above, the electroporation chamber 172 of FIGS. 9 and 10 is designed such that the suspension to be subjected to electroporation enters the electroporation chamber 172 through the fluid inlet 204 and expands to fill the internal chamber 210. As the red blood cells suspension flows through the internal chamber 210, a pulse or charge is administered across the width of the internal chamber 210 between the electrodes 202. To maintain a relatively constant temperature during the electroporation process, cooling fluid or cooling gas is pumped in the cooling inlet 212 and out the cooling outlet 214 of the electrodes 202 through the connectors 208 and 209 so that the electrodes 202 are maintained at approximately 4° C. It is also possible that the inlet channel 204, outlet channel 206 and connectors 208 and 209 can be made as a solidly integrated glass part, rather than separate components.

It is contemplated that the flow electroporation chamber 172 maybe constructed from drawn glass or any other highly polished material. It is preferable that the interior surface of the electroporation chamber 172 be as smooth as possible to reduce the generation of surface turbulence. Drawn glass components are highly consistent with perfect surface finishes. Furthermore, they are stable and inert to blood components. They are also relatively inexpensive, which is desirable for a disposable electroporation chamber.

The electrodes may also be comprised of drawn glass electroplated with colloidal gold. Again, the surfaces of the electrodes should be highly finished, highly conductive, yet biologically inert. Gold electroplate is durable and inexpensive. Fluidic connection can be accomplished using commonly available parts. Alternatively, the electrodes may be coated with crystalline (i.e. titanium nitride), or non-crystalline (i.e. polyethylene glycol) polymers.

The flow electroporation chamber may be constructed either as a part of the entire flow encapsulation apparatus, or as an individual apparatus. The flow electroporation apparatus may then be connected to a commercially available plasmaphoresis machine for encapsulation of particular cell populations. For example, the flow electroporation chamber may be connected to commercially available plasmaphoresis equipment by electronic or translational hardware or software. Optionally, a pinch-valve array and controller driven by a PC program can also be used to control the flow electroporation apparatus. Similarly, current power supplies are capable of establishing the power levels needed to run the flow electroporation chamber or flow encapsulation apparatus.

A third embodiment of a continuous flow electroporation chamber will now be described with reference to FIGS. 14–20. Referring first to FIGS. 14–16, a support member 300 is comprised of flexible silicone rubber. The support structure 300 is essentially diamond shaped and comprises an upper end 301 and a lower end 302. A major portion of the support structure 300 has a grid-like "waffle" pattern formed on it, comprised of thicker rib sections 303 and thinner sections 304 intermediate the ribs 303. Along the marginal edges of the support structure 300, a plurality of tabs 305 are provided, each having a hole 306 formed therethrough.

A channel 308 extends between the upper end 301 and the lower end 302 of the support structure and lies along the major axis of the support structure 300. The channel 308 comprises opposed channel walls 310, 312 connected by a base 314. At the upper end 301 of the support structure 300 the channel 308 opens into a circular cavity 318. A hole 320 is formed in the center of the circular cavity 318. An outlet aperture 322 is provided at the upper end of the circular cavity 318. In a like manner, the lower end of the channel 308 opens into a circular cavity 324 formed in the lower end 302 of the support structure 300. A hole 326 is formed through the support structure in the center of the cavity 324, and an inlet aperture 328 is provided at the lower end of the circular cavity 324.

A pair of continuous band electrodes 330A, 330B comprised of conductive metallic tape or foil are located on the support structure 300. In an alternatively preferred embodiment the electrodes are configured into straight rods. Each of the electrodes 330A, 330B has a portion which is disposed within the channel 308 and which runs substantially the entire length of the channel 308. As can perhaps best be seen in FIG. 16, electrodes 330A, 330B are received in opposing recesses 332 formed in the side walls 310, 312 of the channel 308. Adjacent the upper and lower ends of the channel 308, each of the continuous band electrodes 330A, 330B exits the channel 308 through a close fitting slit formed in the channel walls. The continuous band electrodes 330A, 330B then curve outward and extend substantially parallel to the periphery of the support member 300 and spaced inward therefrom. Along the midline of the support structure 300 and adjacent its outer edges, a slack portion 334 is provided in each of the continuous band electrodes 330A, 330B, for the purposes to be described below.

On either side of the channel 308 and immediately adjacent thereto, a plurality of generally rectangular holes 340 are formed. As will be more fully explained below, the holes 340 are located to optionally accommodate Peltier thermo-electric elements for cooling purposes. On either side of the channel 308 adjacent its upper and lower ends, circular holes 342 are provided which, as will be shown, are adapted to receive capstans for tensioning the continuous band electrodes 330A, 330B. Along the midline of the support structure 300 and adjacent its outer edges, a pair of holes 344 which, as will be more fully explained below, are adapted to receive electrical contacts therethrough for charging the electrodes 330A, 330B.

Referring now to FIG. 17, the support member 300 is mounted to a transparent polycarbonate frame 350. The frame 350 comprises a planar front wall 352. Interior side walls 354 extend rearward from the lateral edges of the planar front wall 352. A rearward opening channel 356 is formed between the two interior side walls 354. At the rear edges of the interior side walls 354, a pair of back walls 358 extend outward. A pair of exterior side walls 360 extend forward from the outer edges of the back walls 358. Forward opening channels 362 are formed between the exterior side walls 360 and the interior side walls 354. Rods 363 removably mounted in each of the forward opening channels 362 provide a convenient means for hanging fluid storage bags within the channels.

The support structure 300 is mounted to the back surface of the front wall 352 of the polycarbonate frame 350. The support structure 300 is adhesively bonded to the frame 350 such that the front wall 352 of the frame 350 seals the open upper end of the channel 308 formed in the face of the support structure 300. Thus enclosed, the channel 308 defines a fluid passage or "flow cell" 364. In addition, the support structure 300 and associated portion of the frame 350 define an electroporation chamber 366.

Referring further to FIG. 17, a support column 370 has a generally rectangular cross section. In the front face 371 of the support column 370 a cavity 372 is formed which conforms to the shape and depth of the support structure 300. Spaced on either side and along the major axis of the cavity 372, a plurality of bismuth telluride Peltier thermoelectric elements 374 are fixedly mounted in the cavity and project forward from the base of the cavity 372. The Peltier thermo-electric elements 374 are in thermal communication with a heat sink 375 mounted inside the support column 370. An electric fan 376 mounted in an adjacent portion of the support column 370 creates a flow of air through the column to dissipate heat away from the heat sink 375.

Adjacent the upper and lower ends of the cavity 372 and spaced to either side of the center line are capstans 377. Adjacent the outer edges of the cavity 372 and located along the minor axis of the cavity are a pair of electrode contacts 378. Located just inside the perimeter of the cavity 372 are eight locator pins 379, two of the locator pins 379 being situated along each of the four walls of the diamond-shaped cavity. At the upper and lower ends of the cavity 372 and located on the major axis of the cavity are a pair of hollow, porous, polymeric cylinders 380. The cylinders 380 are preferably formed of inert foamed polyethylene (such as Porex) with a pore size permitting passage of gas but not liquid. As will be more fully explained hereinbelow, these gas-permeable, liquid impermeable cylinders function as a means for removing bubbles from fluid passing therethrough.

The dimensions of the polycarbonate frame 350 are such that the support column 370 is snugly received within the rearward opening channel 356 of the frame. As the frame 350 is positioned onto the support column 370, the support structure 300 mounted to the back surface of the front wall 352 of the frame 350 fits within the cavity 372 formed in the front face 371 of the support column 370. A shelf 381 is located on the front face 371 of the support column 370 immediately below the cavity 372 to support the lower edge of the polycarbonate frame 350.

With the frame 350 thus mounted to the support column 370, the various elements associated with the cavity 372 and the support column 370 cooperatively engage the support structure 300 as shown in FIG. 19. Specifically, the thermoelectric cooling elements 374 project through the holes 340 in the support structure 300 and contact the walls of the channel 308. The capstans 377 extend through the holes 342 in the upper and lower ends of the support structure 300. The electrode contacts 378 project through the holes 344 in the support structure 300. The locator pins 379 are received within the corresponding holes 306 in the tabs 305 of the support member 300. And the gas-permeable, liquid impermeable cylinders 380 extend through the holes 320, 326 in the cavities 318, 324 at the upper and lower ends 301, 302 of the support structure 300.

Referring now to FIG. 20, at least one of the capstans 377 supporting each of the electrodes 330A, 330B is tensioned such as by tensioning means 382 to maintain the continuous band electrodes in a taut state. As can also be seen in FIG. 20, each electrode contact 378 has a slot 383 formed in its face, and the slack section 334 of the associated continuous band electrode 330A or 330B is threaded through this slot. A motor 384 in driving engagement with each electrode contact 378 can be operated to rotate the electrode contact, thereby winding the electrode 330A or 330B around a portion of the contact and taking up the slack. This winding action serves the additional function of increasing surface contact between the electrode contact 378 and its associated electrode 330A or 330B, thereby enhancing the electrical connection to the electrodes.

The gas permeable, liquid impermeable cylinders 380 at the upper and lower ends of the flow cell 364 (only the upper of which is shown in FIG. 20) are in fluid communication with a vacuum source by way of a coupling 388 and tubing 390. Also shown in FIG. 20, the heat sinks 375 dissipate the heat collected by the thermo-electric cooling elements 374.

Control of fluid flow along the appropriate flow paths into and out of the flow cell 364 is accomplished by peristaltic pumping means 392 and solenoid-activated pinch valves 394, mounted in the support column 350. The pumping means 392 and pinch valves 394 operate under control of appropriate algorithms in computer means (not shown) operably connected thereto.

A cooled plate 396 is mounted on the side of the support column 370. A cooling bag 398 retained in the channel 362 of the frame 350 is held in intimate contact with this plate 396 to cool treated fluids following electroporation. Depending upon the circumstances and the biological substance being treated, the plate 396 may optionally be heated to maintain the contents of the bag 398 at a predetermined temperature above that of the ambient.

Figure 21:
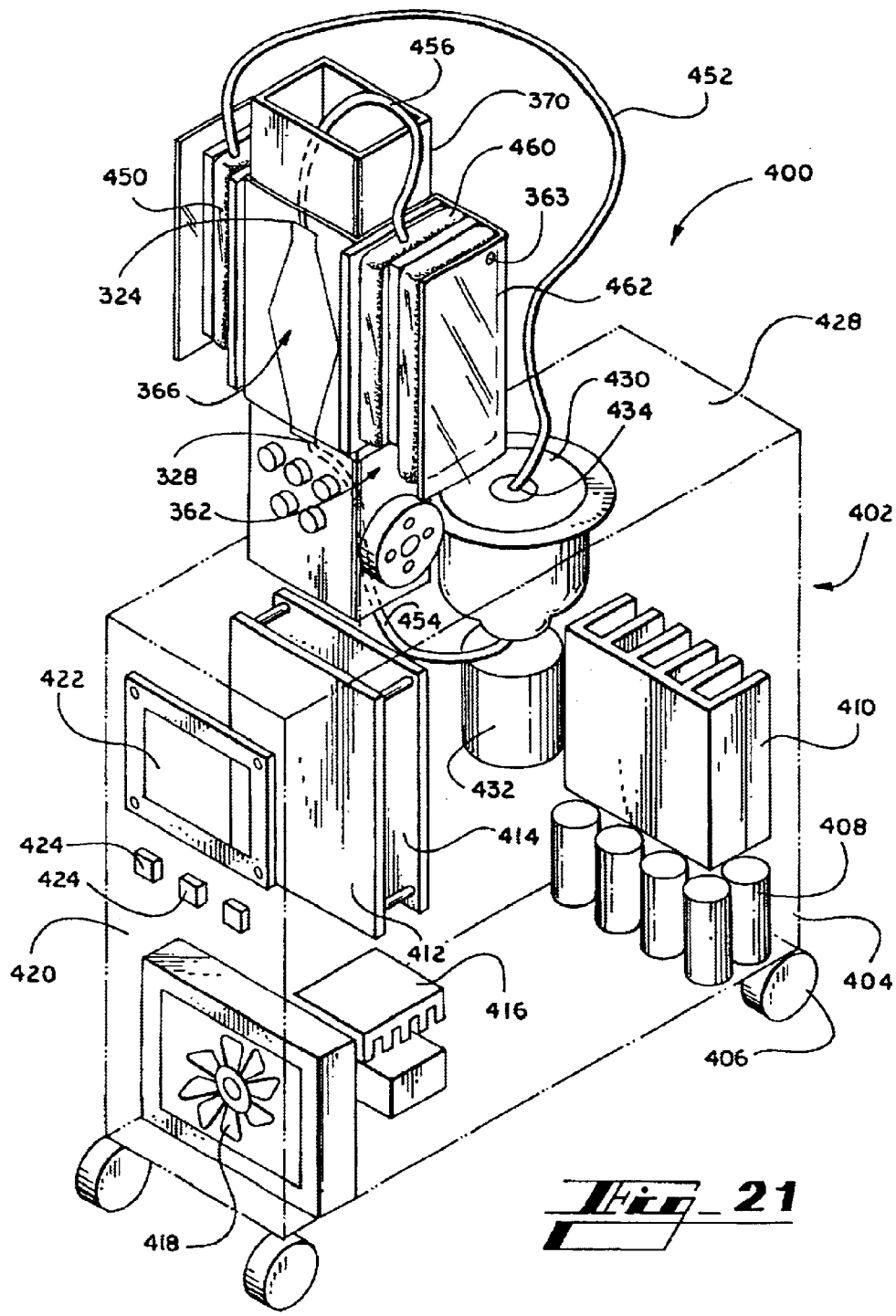
FIG. 21 is a schematic view of a self-contained electroporation apparatus comprising the electroporation chamber of FIGS. 14–20.

FIG. 21 illustrates a self-contained electroporation apparatus 400. The apparatus 400 comprises a cart 402 which serves as a housing and support structure. The support column 370 with electroporation chamber 366 is mounted to the cart and extends upward therefrom. The cart 402 has a chassis structure 404, which is provided with wheels 406 to facilitate transport of the cart 402 from one location to another. Mounted to the chassis structure 404 are power supply capacitors 408. A power supply heatsink 410 is in thermal communication with the power supply capacitors 408 to dissipate the heat generated by the power supply capacitors.

A circuit board computation means 412 is also mounted within the chassis structure 404. The circuit board computation means 412 is powered by a power supply circuit board 414 mounted within the chassis structure 404 adjacent the circuit board computation means. A power supply heatsink 416 in thermal communication with the power supply circuit board 414 dissipates the heat generated by the power supply circuit board. A cooling fan 418 mounted at the lower end of the front panel 420 of the chassis structure 404 pulls air through the chassis structure to draw heat away from the heatsinks 410, 416.

A system status display 422 operatively associated with the circuit board computation means 412 is mounted to the front panel 420 of the cart 402. Control switches 424 for setting various parameters of the circuit board computation means 412 are mounted to the front panel 420 of the cart 402 below the system status display 422.

Mounted within the top panel 428 of the cart 402 is a centrifuge bowl 430. A centrifuge drive motor 432 mounted within the chassis structure 404 is in driving engagement with the centrifuge bowl 430. The centrifuge bowl 430 includes a rotary connector 434 through which blood is input into the centrifuge bowl.

Treatment of biological particles in the self-contained electroporation apparatus 400 comprising the electroporation chamber 366 of the third embodiment will now be described with reference to FIG. 21. A blood supply bag 450 is hung on a rod 363 within one of the channels 362 of the frame 350. A tubing 452 transports the blood to the centrifuge bowl 430, where it is introduced into the centrifuge bowl through a rotary connector 434. The blood is centrifuged to separate the red blood cells from the plasma, white blood cells, and waste. The red blood cells are then admixed with the substance to be encapsulated. The admixture is transported via a tubing 454 and introduced into the inlet aperture 328 at the lower end of the cell 364. The admixture is caused to flow upward through the flow cell 364 between the electrodes 330A, 330B. The electrodes are charged in a pulsed manner, as hereinabove described with respect to the second embodiment. Gases in the admixture resulting from electrolysis are removed by the gas-permeable, liquid impermeable cylinders 380 at the upper and lower ends of the cell. The treated admixture exits the outlet aperture 324 at the upper end of the cell, and an outlet tubing 456 transports the treated admixture to a cooling bag 460 suspended on a rod 363 within another one of the channels 362 of the frame 350 and in contact with the cooled plate 396. The fluid is then conveyed to a post-treatment cooling and storage bag 462 suspended on the rod 363 next to the cooling bag 460.

Pump speeds (and hence flow rates), valve operation, centrifuge operation, operation of the Peltier thermo-electric elements, and pulsed charging of the electrodes are all controlled by the circuit board computation means 412. Ideally, the processing rate of the centrifuge bowl 430 is matched to the flow rate of the flow cell 364. However, to accommodate any mismatch, a reservoir may optionally be provided between the centrifuge bowl 430 and the flow cell 364. Thus if the centrifuge bowl 430 processes the blood faster than the flow cell 364 can process it, the reservoir will hold any excess admixture until the flow cell can "catch up." Similarly, if the centrifuge bowl 430 processes the blood slower than the flow cell 364 can process it, the circuit board computation means 412 can initially accumulate admixture in the reservoir. Then when the centrifuge bowl 430 has processed a sufficient volume of blood, admixture can be transported from the reservoir to the flow cell 364. By the time the volume of admixture in the reservoir has been depleted, the centrifuge bowl will have completed processing the desired quantity of blood.

An optional feature of the electroporation apparatus 400 hereinabove described is that the series of Peltier thermo-electric cooling elements 374 can be individually controllable, such that cooling elements 374 at one location along the flow cell 364 can provide a greater or lesser degree of cooling than other cooling elements 374 at other locations along the flow cell 364. Since the biological particles are being heated as they move along the flow cell 364, more cooling may be necessary closer to the discharge end of the flow cell 364 than is necessary adjacent the input end. Providing individual control over the various thermo-electric cooling elements 374 permits accommodation of these variations. The various thermo-electric cooling elements 374 can be controlled either by placing thermal sensors at various locations along the flow cell, inputting the sensed temperatures into the circuit board computation means 412, and controlling the various thermo-electric cooling elements in response to the sensed temperatures. Or, the various thermo-electric cooling elements 374 can be controlled according to a predetermined "average" temperature variance of the biological particles along the flow cell. Other methods for controlling various thermo-electric cooling elements 374 will occur to those skilled in the art.

As will be appreciated by those familiar with the art, there are several reasons why it is not desirable to re-use an electroporation cell. First, the possibility exists that infectious components could be transferred to other patients. Further, electrical performance of the electrode surfaces would degrade due to the high voltage potentials across these surfaces, thereby increasing the potential for arcing. To prevent these and other problems, a feature of this third disclosed embodiment provides a means for ensuring that the cell is not re-used. At the termination of the procedure, and before the frame 350 is removed from the support column 370, the motors 384 in driving engagement with the electrode contacts 378 are automatically actuated to over-rotate, tensioning the electrodes 330A, 330B beyond their tensile strength and breaking them. With the electrodes 330A, 330B thus broken, re-use of the cell is impossible.

A known risk associated with electroporation apparatus is the unintentional production of gases by electrolysis. Overpressures resulting from the unwanted buildup of such gases have been known to result in explosive expression. To minimize this possibility, the present invention employs a flow cell 364 defined on three sides by soft silicone rubber. In the event of transient overpressures, the elasticity of the support structure 300 will accommodate expansion of the flow cell 364 and thereby reduce the possibility of explosion. In addition, the flow cell 364 is sandwiched tightly between the support column 370 and the polycarbonate frame 350, providing further protection against any possible explosive expression.

While this invention has been described in specific detail with reference to the disclosed embodiments, it will be understood that many variations and modifications may be effected within the spirit and scope of the invention as described in the appended claims.

Cell Washing Apparatus

FIG. 24 is a cutaway schematic view of a cell washing apparatus 500 utilizing filtration dialysis, preferably, counter current filtration dialysis. The intact apparatus has a top and sides which completely contain the internal elements of the apparatus. Another aspect of the present invention is a cell washing apparatus that utilizes counter-current dialysis through a porous membrane to remove the IHP solution and substitute therefore a solution that is compatible with red blood cells including, but not limited to, normal saline. As shown in FIG. 24, the cell washing apparatus 500 comprises a first reservoir 505 which contains cells that have been electroporated. In the case of cells that have been electroporated in the presence of IHP, these cells will have been passed through the electroporation chamber 72 and will be in a solution containing excess IHP. The electroporated cells are then pumped through tubing 515 by pump 510 in the direction of the arrow. The cell suspension are introduced into the cell washing apparatus 500 at tubing entrance 520 which is located in housing cell washing apparatus housing 523. The cell path within the apparatus 500 is defined by a cell plate 526 which has an ridges 525 which define a labyrinth through which the cell suspension will travel.

A preferred labyrinth is shown in FIG. 25 which shows a side view of the cell plate 526 showing the ridges on the plate that define the labyrinth. The cell plate 526 is forced against the first side 577 of a semi-permeable membrane 575 at a force great enough so that the cells are forced along the labyrinth defined by the ridges 525. It is to be understood that the labyrinth defined by the ridges 525 can be any shape so long as the cell suspension is in contact with the semi-permeable membrane 575. The cell suspension is therefore in intimate contact with the semi-permeable membrane 575 while it is passing through the cell washing apparatus 500.

The semi-permeable membrane 575 has pores that are large enough to allow the solution and any dissolved constituents of the solution to pass through the membrane but will not allow the cells in the solution to pass through the membrane. The semipermeable membrane can be any material that is compatible with the cells that are in the cell suspension. Semipermeable membranes that can be used in the cell washing apparatus of the present invention include, but are not limited to, polypropylene (Travenol Laboratories) cellulose diacetate (Asahi Medical), polyvinyl alcohol (Kuraray, polymethylmethacrylate (Toray), and polyvinyl chloride (Cobe Laboratories). For red blood cells, the pores in the semipermeable membrane should be no larger than 1 micron in diameter but may be much smaller in diameter. The cells travel along the labyrinth defined by ridges 525 until the cell suspension exits the apparatus 500 at the exit tube 530. With regard to a cell suspension with IHP therein, the cell suspension is then pumped back to reservoir 505 and is recirculated through the apparatus 500 until the level of IHP in the bathing solution has dropped to an acceptable level.

On the other side of semi-permeable membrane 575, is an identical saline plate 536 which has identical ridges 555 to those ridges on cell plate 526. The saline plate is pushed against the second side 578 of the semi-permeable membrane 575 thereby defining a labyrinth that is the mirror image of the labyrinth defined by ridges 525. A wash solution that is biocompatible with the cells, for example, saline, is pumped from the reservoir 540 containing the biocompatible fluid by pump 565 through tube 567 to cell washing apparatus 500 at wash solution entrance 550.

It is to be understood that the wash solution can be any solution that is biocompatible with the cells that are being washed. This includes, but is not limited to, isotonic saline, hypertonic saline, hypotonic saline, Krebs-Ringer bicarbonate buffer, Earle's balanced salts, Hanks' balanced salts, BES, BES-Tris, HEPES, MOPS, TES, and Tricine. Cell culture media can be used as a wash solution, including, but not limited to, medium 199, Dulbecco's modified eagle's medium, CMRL-1066, minimum essential medium (MEM), and RPMI-1640. In addition, the resealing solutions as defined herein can be used as a wash solution. Finally, any combination of the aforementioned solutions can be used as a wash solution.

The biocompatible solution is pumped through the apparatus by pump 565 following the labyrinth defined by the ridges 555 until the biocompatible solution exits the cell washing apparatus 500 at exit 560. The biocompatible solution is then discarded through drain 570. It is important to note that the apparatus 500 will be most efficient if the biocompatible solution is pumped in an opposite direction to that of the solution containing the cells. However, it is contemplated in this invention that biocompatible solution can be pumped in the same direction as the solution containing the cells.

Using the IHP containing cell suspension from electroporated cells as an example, as both solutions are pumped through cell washing apparatus 500, the cell suspension solution containing the IHP will diffuse through the semi-permeable membrane 575 and, simultaneously, the biocompatible solution, will diffuse in the opposite direction through the semi-permeable membrane 575. As this diffusion continues, the cell suspension solution will gradually be diluted and replaced with the biocompatible solution until the level of IHP is at an acceptable level.

The cell washing apparatus 500 can optionally have a thermal electric element 580 attached to the outside of the cell plate 526 and the outside of wash solution plate 536. It is to be understood that the thermal electric element 580 can be attached to either one or both of the outside of plates 526 and 536. The thermal electric element 580 can be used to cool the solutions or can be used to warm the solutions during the wash cycle. Thus, it is to be understood that if the cell washing apparatus is used with the thermal electric elements attached thereto, the incubator 78 is not required because the cells will be resealed when warmed in the cell washing apparatus which will serve as an incubator. The biocompatible wash solution can be the resealing buffer. It is to be understood that temperature can be controlled by other methods such as a water bath.

The shape of the cell washing apparatus 500 can be any shape including a round container wherein the inner portion of the round container contains the cell suspension and is separated from the outer portion of the round container by the semipermeable membrane 575. The round container 500 could be rotated slowly to help force the solution containing the cells through the semipermeable membrane 575 thereby removing the contaminating material.

The cell washing apparatus can be comprised of any material that is biocompatible with the cells that are to be washed in the apparatus. The cell plate 526 and the wash plate 536 can be manufactured from flexible silicone rubber.

Another embodiment of a cell washing apparatus that can be used to substitute for the centrifuge for washing the electroporated cells is shown in FIG. 26. In this second embodiment of the cell washing apparatus 600, the central feature of the cell washing apparatus is an elastomeric cell 605 which is made from elastomeric material such as silicone rubber. Turning now to FIG. 27, the elastomeric cell 605 is a molded piece with a semi-permeable membrane 610 in the center of the elastomeric cell 605. On either side of the semi-permeable membrane 610 are horizontal indentations 615 which form a labyrinth and run the entire length of the elastomeric cell.

As shown in FIG. 26, the elastomeric cell 605 has inlet port 625 for introducing a wash solution and an outlet port 630 for removing the wash solution and an inlet port 635 for introducing the cells with the electroporation fluid and an outlet port 640 for removing the cells with the electroporation fluid. Thus, the wash solution is introduced on one side of the semipermeable membrane 610 in the elastomeric cell 605, is circulated through the labyrinth and exits at outlet port 640. The electroporation solution containing the electroporated cells is introduced on the other side of the semipermeable membrane 610, is circulated through the labyrinth and exits at outlet port 640.

It is to be understood that the semi-permeable membrane 610 completely separates the two sides and that any communication between the two sides is through the semi-permeable membrane 610. The semi-permeable membrane has pores that allow the solutions to pass through the membrane 610, but does not allow particles, such as cells to pass through the semipermeable membrane 610. The semi-permeable membrane can be any material that is compatible with the cells that are in the cell suspension. Semipermeable membranes that can be used in the cell washing apparatus of the present invention include, but are not limited to, polypropylene (Travenol Laboratories) cellulose diacetate (Asahi Medical), polyvinyl alcohol (Kuraray, polymethylmethacrylate (Toray), and polyvinyl chloride (Cobe Laboratories). For red blood cells, the pores in the semipermeable membrane should be no larger than 1 micron in diameter but may be much smaller in diameter.

The elastomeric cell can be placed into a frame 655 and side 660 can be rotated on hinges 665 and 666 so that the side 660 holds the elastomeric cell 605 against side 665 thereby wedging the elastomeric cell tightly between side 660 and side 665. Side 660 is a thermal electric element which is capable of heating or cooling the elastomeric cell 610. Side 665 is a pulsatile mechanism with a roller 670 which travels on belt 675 and can sequentially squeeze the elastomeric cell as the roller travels around the belt 675 and sequentially puts pressure on flexible rods 677 which run vertically the height of side 665.

In operation, the elastomeric cell is placed into the frame 655 and the side 660 (the thermal electric element) is closed onto the elastomeric cell 605. Of course, the side 660 can be a plate without the thermal electric element. On the first side 615, the inlet is attached to the wash solution tube which is attached to a wash solution reservoir (not shown). Outlet 630 is connected to a drain tube (not shown). On the other side of the elastomeric cell, inlet 635 is connected to the reservoir containing the cells and electroporation fluid (not shown). Outlet 640 is connected to a tube which returns the cells and electroporation fluid to the cell reservoir.

In operation, the peristaltic activator 670 gently pumps on the wash solution side thereby forcing the fluids from the inlet side to the outlet side. Optionally, the two solutions can be pumped through the two labyrinths by external pumps in a manner similar to that shown in cell washing apparatus 500. Because the parastaltic activator is pressing on the elastomeric cell, the transfer of fluid across the semipermeable membrane 650 is enhanced by mass transfer action. This action is continued until the electroporation fluid is essentially replaced by the wash fluid.

Application of IHP Treated Red Blood Cells

The present invention provides a novel method for increasing the oxygen delivering capacity of erythrocytes. In accordance with the method of the present invention, the IHP combines with hemoglobin in a stable way, and shifts its oxygen releasing capacity. Erythrocytes with IHP-hemoglobin can release more oxygen per molecule than hemoglobin alone, and thus more oxygen is available to diffuse into tissues for each unit of blood that circulates. Under ordinary circumstances, IHP is toxic and cannot be tolerated as an ordinary drug. Attachment of IHP to hemoglobin in this novel procedure, however, neutralizes its toxicity. In the absence of severe chronic blood loss, treatment with a composition prepared in accordance with the present method could result in beneficial effects that persist for approximately ninety days.

Another advantage of IHP-treated red blood cells is that they do not lose the Bohr effect when stored. Normal red blood cells that have been stored by conventional means do not regain their maximum oxygen carrying capacity for approximately 24 hours. This is because the DGP in normal red blood cells diffuses away from the hemoglobin molecule during storage and must be replaced by the body after transfusion. In contrast, red blood cells treated according to the present invention are retain their maximum oxygen carrying capacity during storage and therefore can deliver maximum oxygen to the tissues immediately after transfusion into a human or animal.

The uses of IHP-treated RBC's is quite extensive including the treatment of numerous acute and chronic conditions including, but not limited to, hospitalized patients, cardiovascular operations, chronic anemia, anemia following major surgery, coronary infarction and associated problems, chronic pulmonary disease, cardiovascular patients, autologous transfusions, as an enhancement to packed red blood cells transfusion (hemorrhage, traumatic injury, or surgery). congestive heart failure, myocardial infarction (heart attack), stroke, peripheral vascular disease, intermittent claudication, circulatory shock, hemorrhagic shock, anemia and chronic hypoxmia, respiratory alkalemia, metabolic alkalosis, sickle cell anemia, reduced lung capacity caused by pneumonia, surgery, pneumonia, trauma, chest puncture, gangrene, anaerobic infections, blood vessel diseases such as diabetes, substitute or complement to treatment with hyperbaric pressure chambers, intra-operative red cell salvage, cardiac inadequacy, anoxia—secondary to chronic indication, organ transplant, carbon monoxide, nitric oxide, and cyanide poisoning.

Treating a human or animal for any one or more of the above disease states is done by transfusing into the human or animal between approximately 0.5 and 6 units (1 unit= 453 ml±50 ml) of IHP-treated blood that has been prepared according to the present invention. In certain cases, there may be a substantially complete replacement of all the normal blood in a patient with IHP-treated blood. The volume of IHP-treated red blood cells that is administered to the human or animal will depend upon the indication being treated. In addition, the volume of IHP-treated red blood cells will also depend upon concentration of IHP-treated red blood cells in the red blood cell suspension. It is to be understood that the quantity of IHP red blood cells that is administered to the patient is not critical and can vary widely and still be effective.

IHP-treated packed RBC's are similar to normal red blood cells in except that the IHP-treated packed red blood cells can deliver 2 to 3 times as much oxygen to tissue per unit. A physician would therefore chose to administer a single unit of IHP-treated packed red blood cells rather than 2 units of the normal red blood cells. IHP-treated packed red blood cells could be prepared in blood processing centers analogously to the present blood processing methods, except for the inclusion of a processing step where the IHP is encapsulated in the cells.

While this invention has been described in specific detail with reference to the disclosed embodiments, it will be understood that many variations and modifications may be effected within the spirit and scope of the invention as described in the appended claims.

What is claimed is:

1. An apparatus for electroporation, comprising:
   a fluid flow path;
   electrodes disposed along sides of the fluid flow path and configured to subject biological particles moving along the fluid flow path to an electrical field suitable for electroporation; and
   a computer-controllable pump in fluid communication with the fluid flow path and configured to establish a flow rate of the fluid flow path in accordance with a sample processing rate.

2. The apparatus of claim 1, wherein the electrical energy is pulsed.

3. The electroporation chamber of claim 1, wherein the electrical energy is a variable flux.

4. The apparatus of claim 1, wherein the electrodes comprise continuous band electrodes.

5. The apparatus of claim 1, further comprising thermoelectric cooling elements in operative relation with the electrodes.

6. An apparatus for electroporation comprising:

walls defining a fluid flow path;

electrodes disposed along sides of the fluid flow path and configured to subject biological particles moving along the fluid flow path to an electrical field suitable for electroporation; and means for breaking the electrodes prior to the apparatus being removed from the support member whereby the apparatus cannot be re-used.

7. The apparatus of claim 6, wherein:

the electrodes are wrapped around at least a portion of a spindle; and the means for breaking comprise spindles configured to rotate so as to stretch the electrodes beyond their tensile limits to break the electrodes and render them electrically inoperative.

8. An apparatus for electroporation comprising:

walls defining a fluid flow path;

electrodes disposed along sides of the fluid flow path and configured to subject biological particles moving along the fluid flow path to an electrical field suitable for electroporation;

a pump for moving the biological particles along the fluid flow path; and a computer responsive to the rate at which the pump moves the biological particles along the fluid flow path and to the interval between pulses of electrical energy.

9. The apparatus of claim 8, wherein the computer regulates the rate at which the pump moves the biological particles along the fluid flow path.

10. The apparatus of claim 8, wherein the computer regulates the interval between pulses of electrical energy.

11. The apparatus of claim 1, the computer-controllable pump configured to vary the flow rate of the fluid flow path to match the sample processing rate.

12. The apparatus of claim 1, the sample processing rate corresponding to a processing rate of a centrifuge.

13. The apparatus of claim 1, the sample processing rate corresponding to an interval between pulses of electrical energy delivered to the electrodes.

14. The apparatus of claim 1, where one of the walls defining the fluid flow path is elastically deformable and at least another one of the walls defining the fluid flow path is substantially rigid.

15. An apparatus for electroporation, comprising:

a fluid flow path;

electrodes coupled to the fluid flow path and configured to subject biological particles moving along the fluid flow path to an electrical field suitable for electroporation;

a pump configured to establish a flow rate of the fluid flow path; and a computer configured to:
 a. control charging of the electrodes; and
 b. establish a flow rate of the fluid flow path in accordance with a sample processing rate.

16. The apparatus of claim 15, the sample processing rate corresponding to a processing rate of a centrifuge.

17. The apparatus of claim 15, the sample processing rate corresponding to an interval between pulses of electrical energy delivered to the electrodes.

18. The apparatus of claim 15, the computer configured to control the thermoelectric cooling elements individually to cool one location more or less than another location.

19. The apparatus of claim 15, further comprising:

valves configured to control fluid flow;

thermoelectric cooling elements; and wherein the computer is further configured to:
 c. control operation of the valves; or
 d. control the thermoelectric cooling elements.

* * * * *

UNITED STATES PATENT AND TRADEMARK OFFICE
CERTIFICATE OF CORRECTION

PATENT NO. : 6,773,669 B1
DATED : August 10, 2004
INVENTOR(S) : Holaday et al.

It is certified that error appears in the above-identified patent and that said Letters Patent is hereby corrected as shown below:

Column 38,
Line 64, please delete "electroporation chamber" and insert -- apparatus --.

Signed and Sealed this

Eighteenth Day of January, 2005

JON W. DUDAS
*Director of the United States Patent and Trademark Office*